United States Patent
Colledge et al.

(10) Patent No.: US 11,160,793 B2
(45) Date of Patent: Nov. 2, 2021

(54) SOLID DOSAGE FORMS OF BENDAMUSTINE

(71) Applicant: Astellas Deutschland GmbH, Munich (DE)

(72) Inventors: Jeffrey Colledge, Leiderdorp (NL); Thomas Alfred Profitlich, Leiderdorp (NL); Ulrich Patzak, Leiderdorp (NL); Taoufik Ouatas, Leiderdorp (NL); Margaretha Olthoff, Leiderdorp (NL)

(73) Assignee: Astellas Deutschland GmbH, Munich (DE)

( * ) Notice: Subject to any disclaimer, the term of this patent is extended or adjusted under 35 U.S.C. 154(b) by 0 days.

(21) Appl. No.: 15/291,713

(22) Filed: Oct. 12, 2016

(65) Prior Publication Data
US 2017/0100376 A1  Apr. 13, 2017

Related U.S. Application Data

(63) Continuation of application No. 14/717,743, filed on May 20, 2015, now abandoned, which is a continuation of application No. 13/917,144, filed on Jun. 13, 2013, now abandoned, which is a continuation of application No. 13/132,343, filed as application No. PCT/EP2009/008639 on Dec. 3, 2009, now abandoned.

(30) Foreign Application Priority Data

Dec. 3, 2008  (EP) .................................. 08020996

(51) Int. Cl.
| | |
|---|---|
| A61K 9/20 | (2006.01) |
| A61K 31/4184 | (2006.01) |
| A61K 9/28 | (2006.01) |
| A61K 33/243 | (2019.01) |
| A61K 31/437 | (2006.01) |
| A61K 31/573 | (2006.01) |
| A61K 31/704 | (2006.01) |
| A61K 39/395 | (2006.01) |
| A61K 45/06 | (2006.01) |
| A61K 47/26 | (2006.01) |
| A61K 47/30 | (2006.01) |
| A61K 47/36 | (2006.01) |
| A61K 9/00 | (2006.01) |
| A61K 9/48 | (2006.01) |

(52) U.S. Cl.
CPC ........ *A61K 31/4184* (2013.01); *A61K 9/0053* (2013.01); *A61K 9/2009* (2013.01); *A61K 9/2013* (2013.01); *A61K 9/2018* (2013.01); *A61K 9/2054* (2013.01); *A61K 9/282* (2013.01); *A61K 9/284* (2013.01); *A61K 9/2813* (2013.01); *A61K 9/2846* (2013.01); *A61K 9/2853* (2013.01); *A61K 9/4866* (2013.01); *A61K 31/437* (2013.01); *A61K 31/573* (2013.01); *A61K 31/704* (2013.01); *A61K 33/243* (2019.01); *A61K 39/395* (2013.01); *A61K 45/06* (2013.01); *A61K 47/26* (2013.01); *A61K 47/30* (2013.01); *A61K 47/36* (2013.01); *A61K 9/2866* (2013.01); *A61K 9/48* (2013.01)

(58) Field of Classification Search
CPC .................................................. A61K 31/4184
USPC ........................................................ 424/465
See application file for complete search history.

(56) References Cited

U.S. PATENT DOCUMENTS

| | | | |
|---|---|---|---|
| 2006/0058358 A1* | 3/2006 | Dumas | A61K 9/1652 514/350 |
| 2006/0128777 A1* | 6/2006 | Bendall | A61K 31/4184 514/394 |
| 2006/0159713 A1* | 7/2006 | Brittain | A61K 9/0019 424/400 |

FOREIGN PATENT DOCUMENTS

WO   WO 2009/120386 A2 * 10/2009

OTHER PUBLICATIONS

King et al (Remington's Pharmaceutical Sciences, 17th Edition, 1985, Chapter 90, pp. 603-632).*
Jivraj et al (PSTT, 2000, 3(2): 58-63).*

* cited by examiner

*Primary Examiner* — Sean E Aeder
(74) *Attorney, Agent, or Firm* — Morgan. Lewis & Bockius LLP

(57) ABSTRACT

In the present invention there is provided a pharmaceutical composition in a solid dosage form suitable or oral administration, the composition comprising bendamustine or a pharmaceutically acceptable ester, salt or solvate thereof as an active ingredient, and at least one pharmaceutically acceptable excipient, which is a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the saccharide excipient(s) is in the range of 1:1-5.

18 Claims, 2 Drawing Sheets

Flow-sheet of wet granulation manufacturing trials

*Placebo batches were manufactured only for the granulated saccharides with doubtful compression test.

SOLID DOSAGE FORMS OF BENDAMUSTINE

The present invention relates to solid dosage forms for oral administration comprising bendamustine or a pharmaceutically acceptable ester, salt or solvate thereof.

BACKGROUND OF THE INVENTION

Bendamustine (4-[5-[bis(2-chloroethyl)amino]-1-methyl-benzimidazo-2-yl]butanoic acid, a nitrogen mustard) is an alkylating agent with bifunctional alkylating activity. It corresponds to the following formula I:

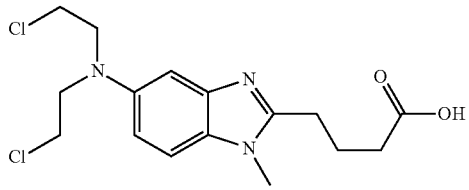

Bendamustine appears to be free of any cross-resistance with other alkylating agents, which offers advantages in terms of chemotherapy for patients who have already received treatment with an alkylating agent.

Bendamustine was initially synthesized in the German Democratic Republic (GDR). The hydrochloric acid of bendamustine was the active ingredient in a commercial product available from 1971 to 1992 under the trade name Cytostasan®. Since that time, it has been marketed in Germany under the trade name Ribomustin® and has been widely used to treat chronic lymphocytic leukemia, non-Hodgkin's lymphoma and multiple myeloma.

The marketed product contains a lyophilized powder of bendamustine hydrochloride which is reconstituted with water for injection yielding a concentrate. This is subsequently diluted with an aqueous solution of 0.9% sodium chloride resulting in the final solution for infusion. This final solution is administered to the patient by intravenous infusion over a period of about 30 to 60 minutes.

Hydrolysis of the bis-2-chloroethylamino-group of bendamustine in water leads to reduction in potency and to impurity formation (B. Maas et al. (1994) in Pharmazie 49: 775-777). Hence administration, usually in a hospital or at least under medical supervision, must occur immediately after reconstitution of the lyophilized powder. Furthermore, reconstitution has been reported to be difficult. It may require more than 30 minutes. Further, it is burdensome and time-consuming for the healthcare professionals responsible for reconstituting the product in the 2 step process.

Preiss et al. (1985) in Pharmazie 40:782-784 compared the pharmacokinetics of bendamustine hydrochloride in plasma in 7 patients after intravenous and oral administration respectively in a dose ranging between 4.2-5.5 mg/kg. The intravenous infusion prepared from the commercially available Cytostasan® product was given over 3 minutes, whereas oral medication in an equivalent dose was taken in the form of capsules, containing 25 mg of bendamustine hydrochloride. The number of capsules to be taken by the patients varied from 10-14. After oral administration maximal plasma levels were detectable within 1 hour. The mean oral bioavailability was calculated to be 57%, ranging from 25% to 94% indicating a large inter-individual variability.

Weber (1991) (Pharmazie 46(8): 589-591) investigated the bioavailability of bendamustine hydrochloride in B6D2F1-mice and found that the absorption of the drug from the gastro-intestinal tract is incomplete resulting in a bio-availability of about 40% only.

US 2006/0128777 A1 describes methods for treating cancers, characterised by death-resistant cells and bendamustine-containing compositions in general. Amongst these compositions are oral solid dosage forms, which are capsules, tablets, pills, powders or granules, wherein the active compound may be admixed with at least one inert excipient, such as sucrose, lactose or starch. However, specific compositions were not exemplified.

In view of the stability problems with the marketed i.v. formulation, once reconstituted with water, and in order to improve the patient compliance there has been a long-felt need for a stable oral dosage-form comprising bendamustine which is easy to administer to the patient and provides an increased bioavailability with less variability as compared to the known oral dosage-form.

SUMMARY OF THE INVENTION

In order to solve the above problems the present inventors have carried out detailed investigations. They finally succeeded in obtaining the stable pharmaceutical compositions according to the invention. These compositions are suitable for oral administration and comprise bendamustine or a pharmaceutically acceptable ester, salt or solvate thereof as an active ingredient, and at least one pharmaceutically acceptable excipient, which compositions have an improved dissolution profile.

DETAILED DESCRIPTION OF THE INVENTION

Figure 1:
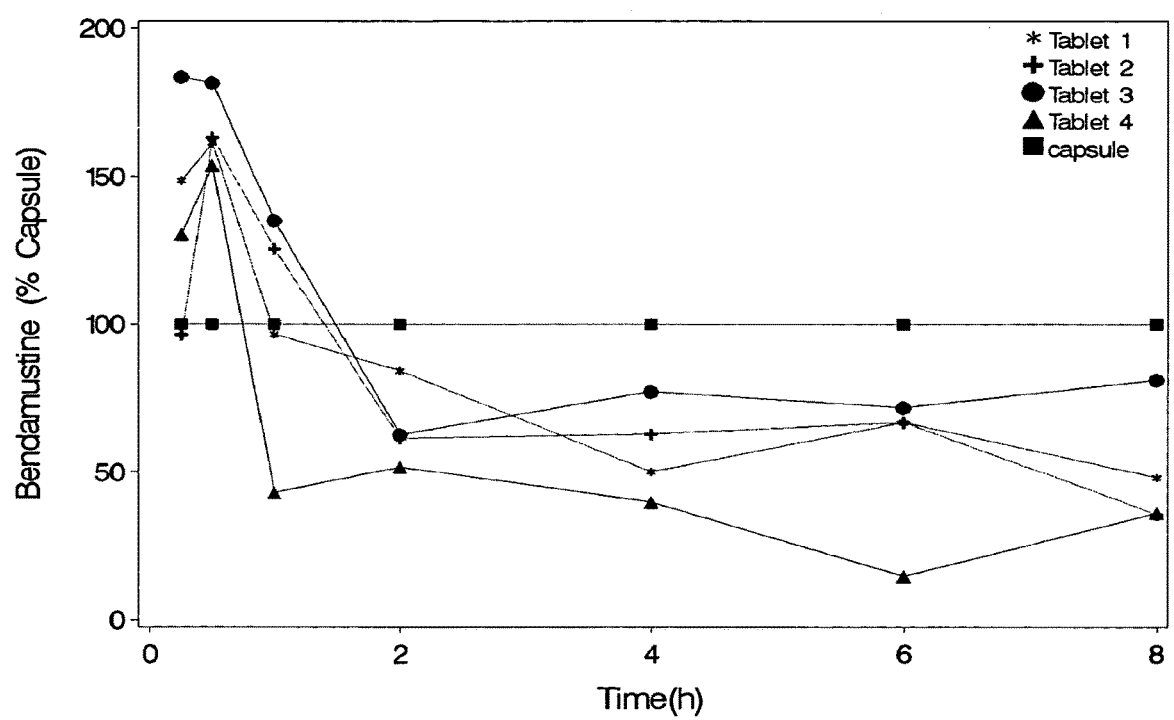
FIG. 1 shows the mean plasma concentration (tablets versus capsule) vs. time curve obtained after administering bendamustine hydrochloride in the form of prior art capsules and the tablet formulations of Examples 6 to 8 (Tablets 1-3) and example 9 (formulation 3) (Tablet 4) to dogs. It is apparent from FIG. 1 that the tablet formulations provide for higher maximum concentrations of bendamustine, as compared to the prior art capsule.

The present invention relates to a pharmaceutical composition comprising bendamustine or a pharmaceutically acceptable ester, salt or a solvate thereof as an active ingredient and at least one pharmaceutically acceptable excipient selected from monosaccharides, disaccharides, oligosaccharides, cyclic oligosaccharides, a polysaccharide and saccharide alcohols. Preferably, the ratio by weight between the active ingredient and excipient is in the range of 1 to 1-5, preferably 1 to 2-5, more preferably a ratio selected from 1:5 and 1:2.

In an embodiment the present invention relates to a pharmaceutical composition in a solid dosage form for oral administration, the composition comprising bendamustine or a pharmaceutically acceptable ester, salt or solvate thereof as an active ingredient, and at least one pharmaceutically acceptable excipient, which is a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the excipient is in the range of 1:1.

In a further embodiment the present invention relates to a pharmaceutical composition in a solid dosage form suitable for oral administration, the composition comprising bendamustine or pharmaceutically acceptable ester, salts or solvates thereof as an active ingredient and at least one pharmaceutically acceptable excipient which is a pharmaceutically acceptable saccharide selected from the group consisting of one or more of a monosaccharide, a disaccharide, an oligosaccharide, a cyclic oligosaccharide, a polysaccharide and a saccharide alcohol, wherein the ratio by weight of the active ingredient to the saccharide excipient (s) is in the range of 1:2-5 and which composition shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

Further preferred embodiments within the scope of the above embodiments are pharmaceutical compositions wherein the pharmaceutically acceptable saccharide is selected from the group consisting of one or more of a monosaccharide, a disaccharide and an oligosaccharide, wherein the ratio by weight of the active ingredient to the saccharide excipient(s) is in the range of 1:2-5 and which composition shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

The present invention is based, inter alia, on the surprising discovery that a specific and desirable dissolution profile can be reached by incorporating a certain amount of pharmaceutically acceptable saccharides into the pharmaceutical composition.

It has been found that if a pharmaceutically acceptable saccharide selected from the group consisting of one or more of a monosaccharide, a disaccharide, an oligosaccharide, a cyclic oligosaccharide, a polysaccharide or a saccharide alcohol and preferably selected from the group consisting of one or more of a monosaccharide, a disaccharide and an oligosaccharide is used as an excipient in a pharmaceutical composition comprising bendamustine or pharmaceutically acceptable ester, salt or solvate thereof as an active ingredient, a particularly favourable profile of the composition as regards stability, tabletting properties, dissolution and impurity formation is achieved. The above saccharides result in a composition which shows a dissolution of the bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

Within the above scope of the invention, any combination of one or more of a monosaccharide, a disaccharide, an oligosaccharide, a cyclic oligosaccharide, a polysaccharide and a saccharide alcohol may be used.

It has particularly been found that particular saccharides are associated with a particularly favourable profile of a pharmaceutical composition as regards stability and dissolution. Preferred saccharides of the composition according to the present invention are dextrose anhydrous, dextrose monohydrate, lactitol monohydrate, trehalose, sorbitol, erythritol, maltose monohydrate, mannitol, lactose anhydrous, lactose monohydrate, maltitol, xylitol, sucrose, sucrose 97%+maltodextrin 3%, β-cyclodextrin, D-raffinose pentahydrate, D-melezitose monohydrate and microcrystalline cellulose. The pharmaceutical compositions according to the present invention show good tabletting characteristics, fast dissolution and a pharmaceutically acceptable stability.

The above saccharides constitute preferred embodiments of the present invention and any combination thereof may be used. Preferably, the ratio between the active ingredient and the above saccharides is in the range of 1:1-5, preferably 1:2-5 and more preferably a ratio selected from 1:5 and 1:2.

A further preferred embodiment of the invention is a pharmaceutical composition in a solid dosage form for oral administration, the composition comprising bendamustine or a pharmaceutically acceptable ester, salt or solvate thereof as an active ingredient and at least one pharmaceutically acceptable excipient selected from dextrose anhydrous, dextrose monohydrate, lactitol monohydrate, trehalose, sorbitol, erythritol, maltose monohydrate, mannitol, lactose anhydrous, lactose monohydrate, maltitol, xylitol, sucrose, sucrose 97%+maltodextrin 3%, β-cyclodextrin, D-raffinose pentahydrate, D-melezitose monohydrate and microcrystalline cellulose and which composition shows a dissolution of the bendamustine of at least 60% in 10 minutes, 70% in 20 minutes and 80% in 30 minutes.

Particularly preferred saccharides are mannitol, maltitol, erythritol, xylitol, lactose, sucrose, glucose, sorbitol, maltose, trehalose, lactitol and dextrose (anhydrous or monohydrate) and the weight ratio of the active ingredient to said saccharide is preferably in the range of 1:2-5. Combinations of two or more saccharides within the scope of the above saccharides are also included within the present invention.

A person skilled in the art is well in a position to select suitable combinations within the saccharide excipients mentioned above and obtain a composition which shows a dissolution of bendamustine of at least 60% in 20 minutes, 70% in 40 minutes and 80% in 60 minutes as measured with a paddle apparatus at 50 rpm according to the European Pharmacopoeia in 500 ml of a dissolution medium at a pH of 1.5.

In a preferred embodiment the composition is in the form of a tablet, a granulate, or a pill.

A preferred dosage form is a tablet. The term tablet also comprises fast-disintegrating tablets, amongst which are dispersible tablets and effervescent tablets.

The most commonly used methods of tablet preparation are direct compression, dry granulation and wet granulation. Direct compression involves compressing a mixture containing the active ingredient(s) and the excipient(s) on a tablet press (L. Lachman et al., in: The Theory and Practice of Industrial Pharmacy, 3rd ed., 1986). The mixture to be compressed must possess both good flow and compression properties in order to produce tablets having a uniform content of the active ingredient(s). Good flow properties cannot always be achieved by adding appropriate excipients, such as lubricants, anti-adhesive agents and flow-promoters to the mixture. Hence frequently the mixture is granulated prior to compression.

Granulation is a process by which sphere-like or regularly shaped aggregates called granules are formed out of the powder mixture. This can be achieved by dry granulation methods and wet granulation methods. Granulation is also used for converting a mixture of powders with poor cohesion into aggregates, which when compressed result in tablets that have good cohesion properties.

In the case of fast-disintegrating tablets, the active ingredient(s), optionally in admixture with one or more excipients, is (are) advantageously provided with a coating in order to mask the taste of such ingredient(s) and/or to protect the same against possible harmful effects by light and/or moisture and in the case of bendamustine to protect the mucosa in the mouth against the harmful effects exerted by the active compound. For that purpose a granulate preferably is prepared and processed as further outlined below.

The expression "granulate" refers to aggregates of particles, sometimes called granules. A granulate in general is prepared by compaction and/or compression techniques (dry granulation) or by wet granulation techniques, using a liquid in which optionally a wet granulation binding agent is dissolved (Remington's Pharmaceutical Sciences 18th ed. 1990, page 1641). Wet granulation techniques also include extrusion techniques. Accordingly the term granulate also comprises pellets, spherules, and extrudates, of which pellets preferably are used as examples of a granulate.

A pellet may be described as a small particle of approximately 1.0-1.6 mm in diameter and having a certain density, which particle is prepared by application of the pharmaceutical processes of extrusion and spheronisation to powder mixtures.

The active ingredient(s), optionally in admixture with one or more excipients, may be advantageously provided with a coating in order to mask the taste of such ingredient and/or to protect the same against possible harmful effects by light and/or moisture and/or to protect the mucosa in the mouth against the harmful effects exerted by the active compound.

Pills are small, round solid dosage forms, prepared by adding the active ingredient to a doughy mixture of triglycerides. The mixture is rolled into a long string, which is then cut into pieces and rolled (J. T. Carstensen: Pharmaceutical principles of solid dosage forms, 1993, Technomic Publishing Company, Inc. page 63).

Preferably the dosage forms according to the invention are prepared by dry compaction techniques. Suitable techniques are for example described in Remington's Pharmaceutical Science 18th. ed. 1990, page 1644. They comprise dry granulation, roller compaction and direct compression. When tablets are prepared by these techniques, it is even more advantageous to use direct compression.

The dosage forms according to the present invention are preferably provided with a coating. The coating has different purposes: it may serve for masking the taste of the active ingredient(s) used in the composition, whilst at the same time it is protecting the active ingredient against possible harmful effects by light and/or moisture such as oxidation, degradation, etc. Furthermore, the coating layer may prevent the subject from damage of the oral mucosa by the active ingredient.

The coating layer can be applied to the dosage forms by techniques well-known in the art such as spray-coating and microencapsulation. For tablets it can be in the form of a film-coating, a saccharide-coating or a compression coating. Preferably a film-coating process is used (Remington's Pharmaceutical Sciences 18th ed. 1990, page 1666). In case an active ingredient requires the application of a coating for fast-disintegrating tablets the individual granules can suitably be provided with a coating prior to compression into tablets.

The expression "pharmaceutically acceptable ester thereof" describes any pharmaceutically acceptable ester of bendamustine, such as esters with alkyl alcohols and saccharide alcohols. Examples of the alkyl alcohols are C1-6-alkyl alcohols such as methanol, ethanol, propanol, isopropanol, butanol and tert-butanol. Examples of the saccharide alcohols are mannitol, maltitol, sorbitol, erythritol, glycol, glycerol, arabitol, xylitol and lactitol. Preferred examples of the bendamustine esters are the ethyl ester, the isopropyl ester, the mannitol ester and the sorbitol ester, most preferred is the ethylester thereof.

The expression "pharmaceutically acceptable salt thereof" describes any pharmaceutically acceptable salt of bendamustine that administered to a patient (directly or indirectly) provides bendamustine. This term further comprises the pharmaceutically acceptable salt of a bendamustine ester. Nevertheless, it will be considered that the pharmaceutically non-acceptable salts also are included within the limits of this invention since these compounds can be useful in the preparation of pharmaceutically acceptable salts. For example, pharmaceutically acceptable salts of bendamustine are synthesized from the corresponding compound that contains an acid or basic group, by conventional chemical methods. Generally, these salts are, for example, prepared by means of the reaction of free acidic or basic forms of these compounds in a stoichiometric amount with a corresponding base or acid in water or an organic solvent or a mixture of both. Nonaqueous media like ether, ethyl acetate, isopropanol or acetonitrile are generally preferred. Examples of acids which may be used for the salt formation of pharmaceutically acceptable salts of bendamustine include inorganic acids such as hydrochloride, hydrobromide, hydriodide, sulphuric, nitric, and phosphoric acids, and organic acids such as acetic, maleic, fumaric, citric, oxalic, succinic, tartaric, malic, lactic, methylsulphonic and p-toluenesulphonic acids. Pharmaceutically acceptable salts of bendamustine may be derived from either inorganic or organic bases to yield ammonium salts; alkali metal salts (lithium, sodium, potassium, etc.), alkaline earth salts like calcium or magnesium, aluminium salts, lower alkylamine salts like methylamine or ethylamine salts, lower alkyldiamine salts like ethylenediamine salts, ethanolamine, N,N-dialkyleneethanolamine, triethanolamine, and glucamine salts, as well as basic salts of amino acids. Especially preferred are acid salts prepared from the hydrochloride, the hydrobromide, and the hydroiodide, whereas the hydrochloride salt is the most preferred pharmaceutically acceptable salt of bendamustine. The pharmaceutically acceptable salts are produced by conventional techniques well-known in the art.

The expression "pharmaceutically acceptable solvate thereof" describes any pharmaceutically acceptable solvate that, administered to a patient (directly or indirectly) provides bendamustine. This term further comprises the pharmaceutically acceptable solvate of a bendamustine ester. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as ethanol is more preferred. A solvent for constituting the solvate is preferably a pharmaceutically acceptable solvent.

It is especially preferred that the active ingredient in the invention's compositions is bendamustine or a pharmaceutically acceptable salt thereof. It is most preferred that the active ingredient is bendamustine hydrochloride.

The dose of the active ingredient in the pharmaceutical composition may readily be determined by the skilled artisan depending on the patient's condition, sex, body weight, body surface area, or age, especially depending on the patient's body weight and body surface area and ranges from 10 to 1000 mg. It is preferred that the daily dosage ranges from about 50 to about 1000 mg, preferably from about 100 to about 500 mg of the active ingredient. The daily dosage may be taken as a single dose or as a multiple dose such as twice or three-times daily, most preferably as a single daily dose. The daily dose may be taken once a week or several times a week. The dosage form may contain the amount of a single daily dose or parts thereof. It is preferred that the dosage form of the present invention comprises about 10 to about 1000 mg, preferably about 25 to about 600 mg, more preferably about 50 to about 200 mg and most preferably about 100 mg of the active ingredient.

The saccharides are present in the compositions according to the invention in a substantial amount, preferably in an amount ranging from 2 to 5 times the weight of the active substance. The saccharides when incorporated into the compositions of the present invention, have shown to have a positive effect on the stability of the active compound. In addition to that it was surprisingly found that these excipients result in an increased bio-availability of the active compound, in particular bendamustine hydrochloride, when compared to the reference capsule.

Preferred examples of the saccharides include mannitol, maltitol, erythritol, xylitol, lactose, sucrose, glucose, sorbitol, maltose, trehalose, lactitol and dextrose (anhydrous or monohydrate).

In addition to these saccharide excipients the pharmaceutical composition according to the present invention may comprise further excipients as described in more detail below for lubricants, glidants, fillers (or diluents), binders and disintegrants.

Lubricants are substances which may have one or more of the following functions in pharmaceutical compositions and especially in tablet manufacture: preventing adhesion of the tablet material to the surface of parts of the tabletting machine (hopper, dies and punches), reducing interparticle friction, facilitating ejection of the tablets from the dies and improving the flow rate of the mixture (to be tabletted). Said lubricant is typically selected from a group consisting of stearic acid, salts or esters of stearic acid, hydrogenated vegetable oils, magnesium oxide, polyethylene glycol, sodium lauryl sulphate and talc, and mixtures thereof. Preferably said lubricant is selected from magnesium stearate, calcium stearate, zinc stearate, glyceryl palmitostearate and sodium stearyl fumarate, and mixtures thereof. Stearic acid is the most preferred alternative.

The term glidant in this application is to be understood as a substance which improves the flow characteristics of the mixture to be tabletted. With respect to glidants, any suitable glidant such as talc, silicon dioxide and silicagel (Cab-O-Sil®, Syloid®, Aerosil®), starch and calcium silicate may be used. Typically, silicon dioxide is used.

Generally, the terms filler (or diluent) represent excipients which are used to increase the bulk of the materials to be tabletted. This increase in size improves the handling of the solid compositions. Fillers are usually necessary if the dose of drug per solid composition is low and the solid composition would otherwise be too small. Examples of suitable fillers are lactose, sucrose, mannitol, sorbitol, saccharose, starch, pregelatinized starch, microcrystalline cellulose, powdered cellulose, calcium hydrogen phosphate, calcium carbonate and any combinations thereof. In a preferred embodiment the filler is selected from the group consisting of lactose, starch, microcrystalline cellulose, microfine cellulose and any combinations thereof, most preferably anhydrous lactose and microcrystalline cellulose.

Generally, the term binder is used for agents that impart cohesiveness to the pharmaceutical formulation, which cohesiveness ensures that the composition remains intact especially in case of tablets after compression. Dependent on the compaction technique used (direct compression, dry granulation or wet granulation) different binders are used. For dry compaction techniques (direct compression and dry granulation) suitable binders are lactose, sucrose, mannitol, sorbitol, saccharose, starch, pregelatinized starch, microcrystalline cellulose, powdered cellulose, calcium hydrogen phosphate, calcium carbonate and any combinations thereof. In a preferred embodiment the binder is selected from the group consisting of lactose, starch, microcrystalline cellulose, microfine cellulose and any combinations thereof, most preferably anhydrous lactose and microcrystalline cellulose. In wet granulation processes binders can be used both as a solution and in a dry form. As suitable binders, there may be mentioned, for example, polyvinylpyrrolidone, dispersible cellulose, hydroxypropyl cellulose, hydroxypropylmethyl cellulose, methylcellulose, starch, pregelatinized starch, partly pregelatinized starch, gum arabic, dextrin, pullulan and the like. Among these binders, dispersible cellulose, polyvinylpyrrolidone, hydroxypropyl cellulose and hydroxypropylmethyl cellulose are more preferred.

A disintegrant can be included in a pharmaceutical composition and especially a tablet composition to facilitate its breakup or disintegration after the tablet comes into contact with a physiological aqueous liquid. When the tablet is swallowed, the disintegrant often is responsible for the quick disintegration of the tablet when it comes into contact with body fluids, such as saliva, gastric and intestinal fluids. Materials serving as disintegrants have been classified chemically as starches, celluloses, cross-linked polymers, etc. As a result of investigations concerning the disintegrator species to be used in the practice of this invention and the level of addition thereof, it was found that starch, a modified starch such as sodium starch glycolate (Primojel®), sodium carboxymethyl cellulose, crosslinked carboxymethylcellulose sodium (Ac-Di-Sol®), cross-linked polyvinylpyrrolidone, polacrilin potassium (Amberlite® IRP88) and low-substituted hydroxypropyl cellulose can produce a very good disintegrating effect.

The stability of an aqueous solution of bendamustine is strongly influenced by the pH. A significant hydrolytic decomposition of this compound is observed at pH values higher than about 5. At pH>5, the decomposition proceeds rapidly and the resulting content of by-products is high in this pH range. The main hydrolysis products are 4-[5-[(2-Chloroethyl)-(2-hydroxy-ethyl)amino]-1-methyl-benzimidazo-2-yl]-butanoic acid (HP1), 4-[5-[Bis(2-hydroxyethyl)amino]-1-methyl-benzimidazo-2-yl]-butanoic acid (HP2) and 4-(5-Morpholino-1-methylbenzimidazol-2-yl)-butanoic acid (HP3):

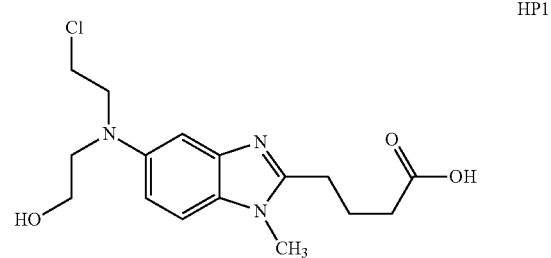

HP1

-continued

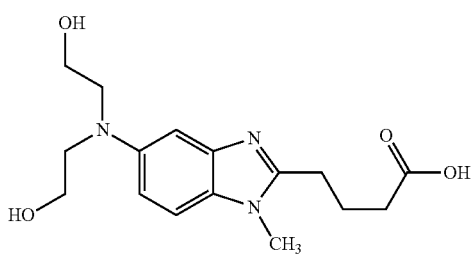
HP2

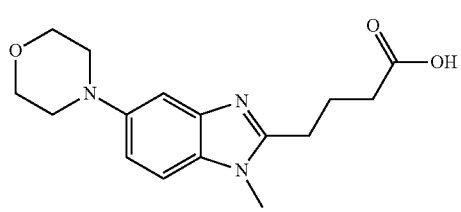
HP3

Absorption of an orally administered drug usually happens in the stomach, the small intestine and/or the large intestine. The pH in the stomach is about 1 to 3.5, in the small intestine about 6.5 to 7.6, and in the large intestine about 7.5 to 8.0. Accordingly, for a compound like bendamustine which is prone to degradation in aqueous environments with a pH higher than 5, it is highly preferable that it is absorbed in the stomach, and does not pass through to the small or even the large intestine, in order to avoid decomposition. Hence there is a need for a pharmaceutical composition from which the bendamustine is absorbed completely or at least to a high extent in the stomach, thereby avoiding or reducing the degradation of the bendamustine in the small or large intestine.

Applicant has found that surprisingly it is possible to solve this problem by using the present pharmaceutical compositions and, in particular, the pharmaceutical composition with the above preferred saccharides. These compositions containing bendamustine show a fast dissolution, and in particular a dissolution of the bendamustine of at least 60% in 20, preferably 10 minutes, 70% in 40, preferably 20 minutes and 80% in 60, preferably 30 minutes, and most preferably of at least 75% in 10 minutes, 85% in 20 minutes and 90% in 30 minutes, as measured with a paddle apparatus at 50 rpm according to the European Pharmacopoeia in an artificial gastric fluid. The artificial gastric fluid as used herein refers to a solution prepared by dissolving 2 g of sodium chloride in 1000 ml of water and then adjusting the pH to 1.5±0.05 with 5 N hydrochloric acid.

The total time of a drug to pass the stomach to the small intestine is between about 20 minutes to 5 hours, usually between about 30 minutes to 3 hours. Thus pharmaceutical compositions according to this invention advantageously should reduce the degradation of bendamustine in the patient since the bendamustine is released and dissolved to a major extent while in the stomach, thus resulting in an improved bioavailability of the bendamustine containing compositions according to the invention.

In a further aspect of this invention the pharmaceutical compositions in a solid dosage form may be used for the treatment, induction, salvage therapy, conditioning prior to stem cell transplantation, maintenance therapy, treatment of residual disease of a medical condition in a human or animal, preferably a human, which medical condition is selected from chronic lymphocytic leukemia (CLL), acute lymphocytic leukaemia (ALL), chronic myelocytic leukaemia (CML), acute myelocytic leukaemia (AML), Hodgkin's disease, non-Hodgkin's lymphoma (NHL), multiple myeloma, breast cancer, ovarian cancer, small cell lung cancer, non-small cell lung cancer, and an autoimmune disease.

The present invention also comprises a method of treatment of a medical condition selected from chronic lymphocytic leukemia, acute lymphocytic leukaemia, chronic myelocytic leukaemia acute myelocytic leukaemia, Hodgkin's disease, non-Hodgkin's lymphoma, multiple myeloma, breast cancer, ovaryian cancer, small cell lung cancer, non-small cell lung cancer, and an autoimmune disease, in a human or animal body comprising administering to the human or animal body in need thereof an effective amount of the pharmaceutical preparation of this invention. Preferably the medical condition is non-Hodgkin's lymphoma.

In another aspect the of this invention the pharmaceutical composition may be administered in combination with at least one further active agent, wherein said further active agent is given prior, concurrently, or subsequently to the administration of the pharmaceutical composition. This at least one further active agent is preferably an antibody specific for CD20 (such as rituximab or ofatumumab), an anthracyclin derivative (such as doxorubicin or daunorubicin), a vinca alkaloid (such as vincristine), a platin derivative (such as cisplatin or carboplatin), daporinad (FK866), YM155, thalidomide and analogues thereof (such as thalidomide or lenalidomide), or a proteasome inhibitor (such as bortezumib).

The pharmaceutical composition of this invention may also be administered in combination with at least one corticosteroid, wherein said corticosteroid is given prior, concurrently, or subsequently to the administration of the pharmaceutical composition. Examples of the corticosteroids are prednisone, prednisolone or dexamthasone.

The following examples further illustrate the invention. It will be apparent to the skilled person that these examples are solely for illustrative purposes and must not be considered to limit the invention.

EXAMPLES

1. Compatibility Tests

Example 1a

For compatibility testing mixtures containing bendamustine hydrochloride and an excipient at a ratio of 1:1 (m/m) were prepared. The excipients were selected from mannitol and lactose. After preparation the mixtures were packed in clear glass HPLC-Vials (6 ml) Agilent and stored at different storage conditions as shown in Table 1 below. At defined time points samples were removed from storage and tested for purity (HPLC; column: Zorbax Bonus-RP, 5 µm; temperature of column oven: 30° C.; temperature of autosampler: 5° C.; detector: 254 nm) and appearance.

TABLE 1

Storage Conditions
Bendamustine hydrochloride and excipients for oral formulation

|  | Tested time points | |
|---|---|---|
| Storage condition | T = 0 | T = 1 month |
| (1) 50° C., Vials closed | n = 2 | n = 1 |
| (2) 70° C., Vials closed* | n = 2 | n = 2 |
| (3) 40° C./75% r.h., Vials open** | n = 2 | n = 2 |

*stored at 50° C. for one month before storage at 70° C.
**stored at 25° C./60% r.h. for one month before storage at 40° C./75%

In all these mixtures, the bendamustine hydrochloride content (measured by HPLC) barely changed and always remained above 99% for all three storage conditions. The hydrolysis product HP1 was barely detectable (Area %<0.2) for all three storage conditions.

Appearance tests of the named bendamustine hydrochloride mixtures were carried out with the naked eye. All the investigated mixtures complied with the specifications and gave white to off-white powder both immediately after preparation and after one month of storage under all three storage conditions.

Example 1b

For further compatibility testing in accordance with the methods of example 1a, mixtures containing bendamustine hydrochloride and an excipient at a ratio of 1:1 (m/m) were prepared. The excipients were selected from Opadry®, Eudragit® E PO, sodium carboxymethylcellulose (Avicel® RC 591) and cross-linked polyvinylpyrrolidone (Crospovidone).

In the case of Eudragit® E PO the initial amounts of the impurities HP1 (hydrolysis product) and BM were significantly increased (HP1:1.5%, BM1DIMER: 1%) but during storage a decrease of these impurities could be detected at all storage conditions independent of the influence of humidity. In the case of cross-linked polyvinylpyrrolidone a significant increase of HP1 from 0.1% to 0.4% could be detected at the storage condition 40°/75% R.H./vials open. At all other storage conditions (vials closed) no increase of HP1 could be detected.

The appearance of the mixtures containing Eudragit® E PO and cross-linked polyvinylpyrrolidone changed at the storage condition 70° C./vials closed. Both mixtures got lightly sticky. Additionally the colour of the mixture with cross-linked polyvinylpyrrolidone changed from white too cream-coloured.

In case of the mixtures containing Opadry® and Avicel® RC591 the colour also changed to cream-coloured at the storage condition 70° C./vials closed.

2. Tablet Formulations

Example 2

253 g of a mixture comprising mannitol as the main excipient and microcrystalline cellulose, Ac-Di-Sol®, colloidal silicon dioxide, talc and stearic acid in the relative quantities mentioned in the following table 2a was prepared by mixing in a 1 liter cube blender (Erweka) for 15 minutes. Thereafter 10.612 g of the mixture and 3.0 g of bendamustine hydrochloride were sieved through a 0.425 mm sieve and then transferred into a Turbula mixer T2A, equipped with a glass vial of 50 ml and subsequently mixed for 10 minutes at 60 rpm.

From this mixture round tablets were compressed having the following characteristics: Mean value diameter: 9.1 mm; mean value mass: 247.7 mg; mean value hardness: 81N.

TABLE 2a

Tablet

| Component | mg/dosage-form | Relative Content % |
|---|---|---|
| bendamustine hydrochloride | 55.1 | 22.04 |
| Mannitol | 141.4 | 56.56 |
| Microcrystalline cellulose (Avicel ® PH112) | 25.0 | 10.00 |
| Ac-Di-Sol ® | 12.5 | 5.00 |
| Colloidal silicon dioxide (Aerosil ® 200) | 1.0 | 0.40 |
| Talc | 12.5 | 5.00 |
| Stearic acid | 2.5 | 1.00 |

Tablets were stored at 40° C./75% RH (glass vial open) or 50° C. (glass vial closed). The amount of bendamustine hydrochloride as well as of related substances, like degradation products, by-products of synthesis were measured with HPLC (column: Zorbax Bonus-RP, 5 μm; temperature of column oven: 30° C.; temperature of autosampler: 5° C.; detector: 254 nm). The results are shown in Table 2b.

TABLE 2b

Related substances and assay of bendamustine HCl (residual content)

| | | | | Bendamustine HCl [% area] | |
|---|---|---|---|---|---|
| Storage condition | Related substances*[1] | T = 0*[2] | T = 1 month | T = 0 | T = 1 month |
| 40° C./75% RH (open vial) | HP1 | 0.13 | 0.22 | 99.60 | 99.13 |
| | NP1 | 0.02 | 0.02 | | |
| | BM1Dimer | 0.06 | 0.25 | | |
| | BM1EE | 0.13 | 0.12 | | |
| | HP2 | n.d. | 0.13 | | |
| | HP3 | n.d. | 0.03 | | |
| 50° C. (closed vial) | HP1 | 0.13 | 0.53 | 99.60 | 98.94 |
| | NP1 | 0.02 | 0.02 | | |
| | BM1Dimer | 0.06 | 0.14 | | |
| | BM1EE | 0.13 | 0.11 | | |
| | HP2 | n.d. | 0.05 | | |
| | HP3 | n.d. | n.d. | | |

*[1]NP1: 4-[6-(2-Chloroethyl)-3,6,7,8-tetra-hydro-3-methyl-imidazo[4,5-h]-[1,4]benzothiazin-2-yl] butanoic acid
BM1Dimer: 4-{5-[N-(2-Chloroethyl)-N-(2-{4-[5-bis(2-chloroethyl)amino-1-methylbenzimidazol-2-yl]butanoyloxy}ethyl)amino]-1-methylbenzimidazol-2-yl}butanoic acid
BM1EE: 4-[5-[Bis(2-chloroethyl)amino]-1-methyl-benzimidazol-2-yl] butanoic ethyl ester
*[2]n.d.: not detectable, i.e. beyond detection limit (area percentage less than 0.05%)

Example 3

A mixture and tablets were prepared in the same way as described in Example 2, but using the compounds and relative amounts as indicated in the following Table 3a.

The tablets had the following characteristics:

Mean value diameter: 9.1 mm; mean value mass: 248.9 mg.

TABLE 3a

Tablet

| Component | mg/dosage-form | Relative Content % |
|---|---|---|
| bendamustine hydrochloride | 55.1 | 22.04 |
| Lactose anhydrous | 141.4 | 56.56 |
| Microcrystalline cellulose (Avicel ® PH112) | 25.0 | 10.00 |
| Ac-Di-Sol ® | 12.5 | 5.00 |
| Colloidal silicon dioxide (Aerosil ® 200) | 1.0 | 0.40 |
| Talc | 12.5 | 5.00 |
| Stearic acid | 2.5 | 1.00 |

Tablets were stored at 40° C./75% RH (glass vial open) or 50° C. (glass vial closed). The amount of bendamustine hydrochloride and of related substances was measured with HPLC as mentioned above. The results are shown in Table 3b:

TABLE 3b

Related substances and assay of bendamustine HCl (residual content)

| | | Bendamustine HCl [% area] | | | |
|---|---|---|---|---|---|
| Storage condition | Related substances | T = 0 | T = 1 month | T = 0 | T = 1 month |
| 40° C./75% RH (open vial) | HP1 | 0.12 | 0.22 | 99.60 | 99.13 |
| | NP1 | 0.02 | 0.02 | | |
| | BM1Dimer | 0.06 | 0.26 | | |
| | BM1EE | 0.13 | 0.13 | | |
| | HP2 | n.d. | 0.11 | | |
| | HP3 | n.d. | 0.03 | | |
| 50° C. (closed vial) | HP1 | 0.12 | 0.57 | 99.61 | 98.88 |
| | NP1 | 0.02 | 0.02 | | |
| | BM1Dimer | 0.06 | 0.13 | | |
| | BM1EE | 0.13 | 0.11 | | |
| | HP2 | n.d. | 0.05 | | |
| | HP3 | n.d. | n.d. | | |

Example 4

Tablets were prepared in the same way as described in Example 2, but using the compounds and relative amounts as indicated in the following Table 4a.

The tablets had the following characteristics:
Mean value diameter: 9.1 mm; mean value mass: 247.8 mg.

TABLE 4a

Tablet

| Component | mg/dosage-form | Relative Content % |
|---|---|---|
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |

Tablets were stored at 40° C./75% RH (glass vial open) or 50° C. (glass vial closed). The amount of bendamustine hydrochloride and of related substances was measured with HPLC as mentioned above. The results are shown in Table 4b:

TABLE 4b

Related substances and assay of bendamustine HCl (residual content)

| | | Bendamustine HCl [% area] | | | |
|---|---|---|---|---|---|
| Storage condition | Related substances | T = 0 | T = 1 month | T = 0 | T = 1 month |
| 40° C./75% RH (open vial) | HP1 | 0.13 | 0.24 | 99.58 | 99.05 |
| | NP1 | 0.02 | 0.02 | | |
| | BM1Dimer | 0.06 | 0.27 | | |
| | BM1EE | 0.14 | 0.13 | | |
| | HP2 | n.d. | 0.13 | | |
| | HP3 | n.d. | 0.06 | | |
| 50° C. (closed vial) | HP1 | 0.13 | 0.63 | 99.58 | 98.32 |
| | NP1 | 0.02 | 0.02 | | |
| | BMlDimer | 0.06 | 0.18 | | |
| | BM1EE | 0.14 | 0.12 | | |
| | HP2 | n.d. | n.d. | | |
| | HP3 | n.d. | n.d. | | |

Prior Art Reference Example 20.0±1 mg of bendamustine hydrochloride were weighed into the body of an empty hard gelatine capsule, and put into a clear glass HPLC vial (6 ml) of Agilent. Capsules were closed by placing the cap on top of the body and slight pushing. Capsules were stored at 40° C./75% RH (glass vial open) or 50° C. (glass vial closed). The amount of bendamustine hydrochloride and of related substances was measured with HPLC as mentioned above. The results are shown in Table 5:

TABLE 5

Related substances and assay of bendamustine HCl (residual content)

| | | Bendamustine HCl [% area] | | | |
|---|---|---|---|---|---|
| Storage condition | Related substances | T = 0 | T = 1 month | T = 0 | T = 1 month |
| 40° C./75% RH (open vial) | HP1 | 0.10 | 0.45 | 99.64 | 98.83 |
| | NP1 | 0.02 | 0.02 | | |
| | BM1Dimer | 0.06 | 0.42 | | |
| | BM1EE | 0.13 | 0.11 | | |
| | HP2 | n.d. | n.d. | | |
| | HP3 | n.d. | n.d. | | |
| 50° C. (closed vial) | HP1 | 0.10 | 1.46 | 99.64 | 97.51 |
| | NP1 | 0.02 | 0.02 | | |
| | BM1Dimer | 0.06 | 0.24 | | |
| | BM1EE | 0.13 | 0.12 | | |
| | HP2 | n.d. | n.d. | | |
| | HP3 | n.d. | n.d. | | |

As is immediately apparent, the capsule formulations were a lot less stable than the tablet formulations according to the invention although the capsule formulations were prepared from pure bendamustine hydrochloride without any further processing steps. Both at 40° C./75% RH (glass vial open) and 50° C. (closed vial) more degradation products are formed within one month of storage. In the case of open vial with 40° C. and 75% RH (relative humidity) the amount of hydrolysis product HP1 is increased by a factor of 4 after one month of storage. For the closed vials the HP1 content is even higher, which might be due to reaction with the capsules. Summarising, tablets provide a much more stable solid dosage form than the capsules.

Example 5

8.0 g of hydroxypropylmethyl cellulose and 1.5 g PEG 6000 are dissolved in 88.5 g purified water. Thereafter 2.0 g yellow ferric oxide and 0.5 g titanium oxide are dispersed therein yielding a coating liquid. Tablets as obtained in Example 2 are coated with 3% of this solution per tablet mass using a film coating device.

Example 6

TABLE 6a

Coated Tablet

| Component | mg/dosage-form | Relative Content % |
|---|---|---|
| Tablet cores | | |
| bendamustine hydrochloride | 55.1 | 21.09 |
| Mannitol | 141.4 | 54.11 |
| Microcrystalline cellulose (Avicel ® PH101) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |
| Film-coating | | |
| Opadry ® | 12.5 | 10 |
| Purified water | — | 90 |
| Target mass gain (mg/tablet)/Sum | 12.5 | 100 |

Manufacturing method for 1000 tablets

All tablet-core components except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the aforementioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics:

Mean value diameter: 9.5 mm; mean value mass: 254.6 mg (begin)-257.2 mg (end); friability 0.1%; mean value hardness: 122N (begin)-128 (end).

The tablets were subsequently film-coated with the Opadry® dispersion until a mass increase of 5% had been achieved.

The mean mass of the film-coated tablets was 268.4 mg.

Both the tablet cores and film-coated tablets were stored at 40° C./75% RH in closed amber glass vials. The amount of bendamustine hydrochloride as well as of related substances, like degradation products, by-products of synthesis were measured with HPLC as mentioned above. The results are shown in Tables 6b.1 and 6b.2.

TABLE 6b.1

Related substances and assay of bendamustine HCl (residual content) in tablet cores

| Storage condition | Related substances | T = 0 | T = 2 months | Bendamustine HCl [% area] T = 0 | T = 2 months |
|---|---|---|---|---|---|
| 40° C./75% RH (closed vials) | HP1 | 0.15 | 0.13 | 99.49 | 99.49 |
| | NP1 | n.d. | n.d. | | |
| | BM1Dimer | 0.09 | 0.17 | | |
| | BM1EE | 0.15 | 0.13 | | |
| | Unid RRT 0.69*³ | 0.08 | 0.05 | | |

*³Unidentified compound peak at relative retention time of 0.69 as compared to main peak

TABLE 6b.2

Related substances and assay of bendamustine HCl (residual content) in coated tablet

| Storage condition | Related substances | T = 0 | T = 2 months | Bendamustine HCl [% area] T = 0 | T = 2 months |
|---|---|---|---|---|---|
| 40° C./75% RH (closed vials) | HP1 | 0.16 | 0.17 | 99.46 | 99.29 |
| | HP2 | n.d. | 0.08 | | |
| | HP3 | n.d. | <0.05 | | |
| | NP1 | n.d. | n.d. | | |
| | BM1Dimer | 0.09 | 0.18 | | |
| | BM1EE | 0.15 | 0.14 | | |
| | Unid RRT 0.69 | 0.10 | 0.05 | | |

Example 7

TABLE 7a

Tablet

| Component | mg/dosage-form | Relative Content % |
|---|---|---|
| Tablet cores | | |
| bendamustine hydrochloride | 55.1 | 21.09 |
| Lactose anhydrous | 141.4 | 54.11 |
| Microcrystalline cellulose (Avicel ® PH112) | 25.0 | 9.57 |
| Crosscarmellose sodium (Ac-Di-Sol ®) | 12.5 | 4.78 |
| Colloidal silicon dioxide (Aerosil ® 200) | 1.0 | 0.38 |
| Talc | 18.8 | 7.19 |
| Stearic acid | 7.5 | 2.87 |
| Sum | 261.3 | 100 |
| Film-coating | | |
| Eudragit ® E PO | 7.5 | 7.5 |
| Sodium laurylsulphate | 0.8 | 0.8 |
| Stearic acid | 1.2 | 1.2 |
| Iron oxide | 1.0 | 1.0 |
| Titanium dioxide | 1.0 | 1.0 |
| Talc | 3.5 | 3.5 |
| Purified water | — | 85.0 |
| Target mass gain (mg/tablet)/Sum | 15.0 | 100.0 |

Manufacturing method for 1000 tablets

All tablet-core components except for colloidal silicon dioxide and stearic acid were loaded into a Somakon vessel (5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the aforementioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics: mean value diameter: 9.5 mm; mean value mass: 262.4 mg (begin)-254.4 mg (end); friability: 0.1% (begin)-0.2% (end); mean hardness value: 98N (begin)-91N (end). The tablets were subsequently film-coated with the Eudragit® dispersion until a mass increase of 3% had been achieved.

The mean mass of the film-coated tablets was 273.5 mg.

Both the tablet cores and the film-coated tablets were stored at 40° C./75% RH in closed amber glass vials. The amount of bendamustine hydrochloride and of related substances was measured with HPLC, as mentioned above. The results are shown in Tables 7b.1 and 7b.2:

TABLE 7b.1

Related substances and assay of bendamustine HCl (residual content) in tablet core

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.17 | 0.12 | 99.50 | 99.55 |
| | NP1 | n.d. | n.d. | | |
| | BM1Dimer | 0.09 | 0.14 | | |
| | BM1EE | 0.15 | 0.14 | | |
| | Unid RRT 0.69 | 0.06 | <0.05 | | |

TABLE 7b.2

Related substances and assay of bendamustine HCl (residual content) in coated tablet

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.18 | 0.20 | 99.43 | 98.93 |
| | HP2 | n.d. | 0.35 | | |
| | HP3 | n.d. | 0.07 | | |
| | NP1 | n.d. | n.d. | | |
| | BM1Dimer | 0.12 | 0.20 | | |
| | BM1EE | 0.15 | 0.13 | | |
| | Unid RRT 0.69 | 0.05 | <0.05 | | |

Example 8

TABLE 8a

| Tablet | | |
|---|---|---|
| Component | mg/dosage-form | Relative Content % |
| Tablet cores | | |
| Bendamustine hydrochloride | 55.1 | 22.04 |
| Lactose anhydrous | 145.15 | 58.06 |
| Microcrystalline cellulose (Avicel ® PH112) | 31.25 | 12.50 |
| Ac-Di-Sol ® | 12.5 | 5.00 |
| Colloidal silicon dioxide (Aerosil ® 200) | 1.0 | 0.40 |
| Magnesium stearate | 2.5 | 1.00 |
| Ascorbic acid | 2.5 | 1.00 |
| Sum | 250 | 100.0 |
| Film-coating | | |
| Eudragit ® E PO | 7.5 | 7.5 |
| Sodium laurylsulphate | 0.8 | 0.8 |
| Stearic acid | 1.2 | 1.2 |
| Iron oxide | 1.0 | 1.0 |
| Titanium dioxide | 1.0 | 1.0 |
| Talc | 3.5 | 3.5 |
| Purified water | — | 85.0 |
| Target mass gain (mg/tablet)/Sum | 15.0 | 100.0 |

Manufacturing method for 1000 tablets

All tablet-core components except for colloidal silicon dioxide and stearic acid were loaded into a Somakon vessel (2.5 L). Bendamustine was added and blending was conducted for 4 minutes at 1000 rpm (wiper 10 rpm). The resulting blend was sieved through a 0.5 mm sieve. The vessel was reloaded with the blend and colloidal silicon dioxide was added. Blending was conducted for 2 minutes at the afore-mentioned conditions. Thereafter stearic acid was added and blending was continued for 1 minute. The blend was subsequently sieved through a 0.5 mm sieve, reloaded into the vessel and blended for another 30 seconds, all at the same conditions.

From this mixture round tablets were compressed having the following characteristics: Mean value diameter: 9.5 mm; mean value mass: 252.2 mg (begin)-250.7 mg (end); friability: 0.1% (begin)-0.2% (end); mean hardness value: 65N (begin)-73N (end). The tablets were subsequently film-coated with the Eudragit® dispersion until a mass increase of 3% had been achieved.

The mean mass of the film-coated tablets was 253.6 mg.

Both the tablet cores and the film-coated tablets were stored at 40° C./75% RH in closed amber glass vials. The amount of bendamustine hydrochloride and of related substances was measured with HPLC, as described above. The results are shown in Tables 8b.1 and 8b.2:

TABLE 8b.1

Related substances and assay of bendamustine HCl (residual content) in tablet core

| Storage condition | Related substances | T = 0 | T = 2 months | T = 0 | T = 2 months |
|---|---|---|---|---|---|
| | | | | Bendamustine HCl [% area] | |
| 40° C./75% RH (closed vials) | HP1 | 0.17 | 0.14 | 99.47 | 99.45 |
| | HP3 | n.d. | 0.07 | | |
| | NP1 | n.d. | n.d. | | |

TABLE 8b.1-continued

Related substances and assay of bendamustine
HCl (residual content) in tablet core

| Storage condition | Related substances | Bendamustine HCl [% area] | | | |
|---|---|---|---|---|---|
| | | T = 0 | T = 2 months | T = 0 | T = 2 months |
| | BM1Dimer | 0.10 | 0.19 | | |
| | BM1EE | 0.15 | 0.14 | | |
| | Unid RRT 0.69 | 0.05 | n.d. | | |

TABLE 8b.2

Related substances and assay of bendamustine
HCl (residual content) in coated tablet

| Storage condition | Related substances | Bendamustine HCl [% area] | | | |
|---|---|---|---|---|---|
| | | T = 0 | T = 2 months | T = 0 | T = 2 months |
| 40° C./75% RH (closed vials) | HP1 | 0.19 | 0.16 | 99.46 | 99.36 |
| | HP2 | n.d. | 0.06 | | |
| | HP3 | n.d. | 0.05 | | |
| | NP1 | n.d. | n.d. | | |
| | BM1Dimer | 0.09 | 0.18 | | |
| | BM1EE | 0.15 | 0.14 | | |
| | Unid RRT 0.69 | <0.05 | <0.05 | | |

Example 9

TABLE 9a composition coated tablets

| component | Composition | | |
|---|---|---|---|
| | PF1 mg/tablet | PF2 mg/tablet | PF3 mg/tablet |
| Bendamustine HCl | 55.1 | 55.1 | 55.1 |
| Anhydrous dextrose | — | — | 205.8 |
| Dextrose monohydrate | 186.0 | — | — |
| Trehalose | — | 66.0 | — |
| sorbitol | — | — | 43.9 |
| Lactose DCL 21 | 68.2 | 185.7 | — |
| Avicel ® PH 112 | 18.7 | — | 23.0 |
| Crospovidone | — | 21.0 | — |
| Magnesium stearate | 2.0 | 2.2 | 2.2 |
| Opadry | 8.0 | 8.0 | 8.0 |
| Total | 338.0 | 338.0 | 338.0 |

Manufacturing method for formulations PF1 for 600 tablets:

33.06 g of bendamustine, 111.60 g of dextrose, 40.92 g of lactose, 11.22 g of microcrystalline cellulose and 1.20 g of magnesium stearate were weighed and transferred into a double polyethylene bag and mixed for 5 minutes. Thereafter the powder blend was transferred to the hopper of an eccentric tabletting machine (Korsch EK0) and compressed into round tablets having the following characteristics: mean value diameter: 10.0 mm; mean value mass: 336.9 mg (begin)-335.98 (end); friability: 0.15%; mean hardness value: 69.25N (begin)-68.60N (end).

The tablet cores were subsequently coated in a coating pan (4M8 ForMate PanCoat) using a 9% Opadry® White aqueous suspension and dried. The mean mass of the tablets was 342.42 mg. Thereafter the tablets were packed into amber glass bottles closed with screw plugs and stored at 40° C./75% RH.

Manufacturing method for formulations PF2 for 600 tablets:

33.06 g of bendamustine, 111.42 g of lactose, 39.60 g of trehalose, 12.60 g of cross-linked polyvinylpyrrolidone and 1.32 g of magnesium stearate were weighed and transferred into a double polyethylene bag and mixed for 5 minutes. Thereafter the powder blend was transferred to the hopper of an eccentric tabletting machine (Korsch EK0) and compressed into round tablets having the following characteristics: mean value diameter: 10.0 mm; mean value mass: 332.95 mg (begin)-332.12 (end); friability: 0.3%; mean hardness value: 65.9 N (begin)-59.0 N (end).

The tablet cores were subsequently coated in a coating pan (4M8 ForMate PanCoat) using a 9% Opadry® White aqueous suspension and dried. The mean mass of the tablets was 340.1 mg. Thereafter the tablets were packed into amber glass bottles closed with screw plugs and stored at 40° C./75% RH.

Manufacturing method for formulation PF3:

Sorbitol and anhydrous dextrose were weighed. 140.64 g of Sorbitol was dissolved in 105.48 g of purified water and the solution obtained was subsequently used to granulate 659.36 g of dextrose in a Fluid Bed Granulator (4M8ForMate FluidBed). Thereafter the granulate was dried at 60° C. and sieved through a 850 μm sieve.

33.06 g of bendamustine hydrochloride, 149.82 g of the sorbitol/dextrose granulate, 13.8 g of microcrystalline cellulose and 1.32 g of magnesium stearate were weighed into a double polyethylene bag and mixed for 5 minutes. Thereafter the powder blend was transferred to the hopper of an eccentric tabletting machine (Korsch EK0O and compressed into round tablets having a mean diameter of 10.0 mm. The tablets had a mean value for mass of 335.99 mg (begin)-339.50 mg (end); friability: 0%; mean hardness value: 125.60N (begin)-129.7N (end). The tablets were then subjected to a conditioning process according to the following two steps (performed only on selected batches): placing them at 25° C./60% R.H. for two hours and subsequently at 40° C. for two hours.

The tablets were subsequently coated in a coating pan (4M8 ForMate PanCoat) using a 9% Opadry® White aqueous suspension. Mean mass of the tablets: 341.43 mg. Thereafter the tablets were packed into amber glass bottles closed with screw plugs and stored at 40° C./75% RH.

The amount of bendamustine hydrochloride and of related substances in the stored film-coated tablets was measured with HPLC, as described above. The results are shown in Tables 9b.1-9b.3:

TABLE 9b.1

Related substances and assay of bendamustine HCl (residual content)
in coated tablet (formulation 1; Opadry ®) PF1

| Storage condition | Related substances | Bendamustine HCl [% area] | | | |
|---|---|---|---|---|---|
| | | T = 0 | T = 3 months | T = 0 | T = 3 months |
| 40° C./75% RH (closed vials) | HP1 | 0.03 | 0.08 | 99.5 | 98.7 |
| | NP1 | n.d. | n.d. | | |
| | BM1Dimer | 0.05 | 0.16 | | |
| | BM1EE | 0.15 | 0.13 | | |
| | Individual | 0.01 | 0.06 | | |

TABLE 9b.1-continued

Related substances and assay of bendamustine HCl (residual content) in coated tablet (formulation 1; Opadry ®) PF1

| Storage condition | Related substances | T = 0 | T = 3 months | T = 0 | T = 3 months |
|---|---|---|---|---|---|
| | | | Bendamustine HCl [% area] | | |
| | unknown impurity | | | | |

TABLE 9b.2

Related substances and assay of bendamustine HCl (residual content) in coated tablet (formulation 2; Opadry ®) PF2

| Storage condition | Related substances | T = 0 | T = 3 months | T = 0 | T = 3 months |
|---|---|---|---|---|---|
| | | | Bendamustine HCl [% area] | | |
| 40° C./75% RH (closed vials) | HP1 | 0.02 | 0.23 | 98.5 | 98.3 |
| | NP1 | 0.01 | 0.01 | | |
| | BM1Dimer | 0.03 | 0.23 | | |
| | BM1EE | 0.15 | 0.11 | | |
| | Individual unknown impurity | 0.01 | 0.05 | | |

TABLE 9b.3

Related substances and assay of bendamustine HCl (residual content) in coated tablet (formulation 3; Opadry ®) PF3

| Storage condition | Related substances | T = 0 | T = 3 months | T = 0 | T = 3 months |
|---|---|---|---|---|---|
| | | | Bendamustine HCl [% area] | | |
| 40° C./75% RH (closed vials) | HP1 | 0.05 | 0.09 | 98.1 | 98.4 |
| | NP1 | n.d. | n.d. | | |
| | BM1Dimer | 0.06 | 0.19 | | |
| | BM1EE | 0.15 | 0.14 | | |
| | Individual unknown impurity | 0.03 | 0.11 | | |

3. Dissolution Tests

Example 10

Dissolution tests for the tablet formulations of Examples 2 and 3 were carried out in artificial gastric fluid at T=0. The dissolution samples are tested for assay by HPLC (column: Zorbax Bonus-RP, 5 μm; temperature of column oven: 30° C.; temperature of autosampler: 5° C.; detector: 254 nm). Artificial gastric fluid pH 1.5 was prepared by dissolving 2 g of sodium chloride p.A. in 1000 ml of water and adjusting the pH to 1.5±0.05 with 5 N hydrochloric acid. The dissolution test was conducted according to Chapter 2.9.3. of European Pharmacopoeia 6.0, using Apparatus 2 (Paddle-apparatus). The rotation speed of the paddle was 50 rpm, the temperature was 37° C.±0.5° C., the amount of dissolution medium was 500 ml.

The results for the tablet formulations of Example 2 (tablet formulation 1) and Example 3 (tablet formulation 2) are shown in the following Table 10a:

TABLE 10a

| Dissolution after: | Tablet formulation 1 Dissolution | | Tablet formulation 2 Dissolution: | |
|---|---|---|---|---|
| | Single value [%] | Mean value [%] | Single value [%] | Mean value [%] |
| 10 min | 85.3 | 84 | 80.9 | 88 |
| | 77.4 | | 87.8 | |
| | 87.2 | | 88.7 | |
| | 90.6 | | 94.3 | |
| | 79.6 | | 87.9 | |
| | 84.1 | | 90.8 | |
| 20 min | 94.7 | 95 | 96.5 | 96 |
| | 95.7 | | 98.7 | |
| | 96.6 | | 95.7 | |
| | 96.4 | | 94.3 | |
| | 93.0 | | 93.8 | |
| | 93.9 | | 97.0 | |
| 30 min | 93.3 | 94 | 95.3 | 95 |
| | 94.3 | | 96.4 | |
| | 95.4 | | 94.4 | |
| | 95.4 | | 93.1 | |
| | 91.8 | | 92.9 | |
| | 93.0 | | 95.3 | |

The results of the same dissolution tests carried out on the coated tablet formulations of Example 6, Example 7 and Example 8 at T=0 are shown in the following Table 10b:

TABLE 10b

| Dissolution after | Tablet formulation example 6 Mean value | Tablet formulation example 7 Mean value | Tablet formulation example 8 Mean value |
|---|---|---|---|
| 10 minutes | 77 | 47 | 83 |
| 20 minutes | 88 | 76 | 90 |
| 30 minutes | 87 | 87 | 88 |

Corresponding dissolution data for the tablets of example 9 were:

| Dissolution after | Tablet formulation example 9 (PF1) Mean value after 3 months at 40° C./75% RH | Tablet formulation example 9 (PF2) Mean value after 3 months at 40° C./75% RH | Tablet formulation example 9 (PF3) Mean value after 3 months storage at 40° C./75% RH |
|---|---|---|---|
| 10 minutes | 89.7 | 96.3 | 60.1 |
| 20 minutes | 93.7 | 95.2 | 88.8 |
| 30 minutes | 93.2 | 93.3 | 94.0 |

As may be taken from the above all tablet formulations of the invention show a fast dissolution of bendamustine. In particular the inventive formulations show a dissolution profile of the bendamustine as defined hereinbefore.

4. In Vivo Tests

Animal Bioavailability Studies of Bendamustine were Performed in Beagle Dogs: PK Study Outlines Study 1

The objective was to determine the bioavailability of 1 dose (i.e. 50 mg) of bendamustine in 3 tablet formulations (T1-3) and 1 capsule formulation (C) with a total of 4 oral formulations: AUC and Cmax Total number of animals required: 16
Basic Design:
Cross-Over Design, 8 Animals Per Arm:

TABLE 11a

| Period 1 (single dose of tablet, or capsule, day 1): | | | | | |
|---|---|---|---|---|---|
| Group | Treatment | Dose route | Dose (mg) | # Number of animals | Animal numbers |
| 1 | Bendamustine | Capsule | 50 | 2 Male + 2 Female | 37, 39 38, 40 |
| 2 | Bendamustine | Tablet T1 | 50 | 2 Male + 2 Female | 41, 43 42, 44 |
| 3 | Bendamustine | Capsule | 50 | 1 Male + 1 Female | 45 46 |
| 4 | Bendamustine | Tablet T2 | 50 | 2 Male + 1 Female | 47, 49 48 |
| 5 | Bendamustine | Tablet T3 | 50 | 1 Male + 2 Female | 51 50, 52 |

One Week Wash-Out

TABLE 11b

| Period 2 (1 week after period 1, single dose of any of the following, day 8): | | | | | |
|---|---|---|---|---|---|
| Group | Treatment | Dose route | Dose (mg) | # Number of animals | Animal numbers |
| 1 | Bendamustine | Tablet T1 | 50 | 2 Male + 2 Female | 37, 39 38, 40 |
| 2 | Bendamustine | Capsule | 50 | 2 Male + 2 Female | 41, 43 42, 44 |
| 3 | Bendamustine | Tablet T3 | 50 | 1 Male + 1 Female | 45 46 |
| 4 | Bendamustine | Capsule | 50 | 2 Male + 1 Female | 47, 49 48 |
| 5 | Bendamustine | Tablet T2 | 50 | 1 Male + 2 Female | 51 50, 52 |

One Week Wash-Out

TABLE 11c

| Period 3 (1 week after period 2, single dose of any of the following, day 15): | | | | | |
|---|---|---|---|---|---|
| Group | Treatment | Dose route | Dose (mg) | # Number of animals | Animal numbers |
| 3 | Bendamustine | Tablet T2 | 50 | 1 Male + 1 Female | 45 46 |
| 4 | Bendamustine | Tablet T3 | 50 | 2 Male + 1 Female | 47, 49 48 |
| 5 | Bendamustine | Capsule | 50 | 1 Male + 2 Female | 51 50, 52 |

Study 2

The objective was to determine the bioavailability of 1 dose (i.e. 50 mg) of bendamustine in 1 tablet formulation T4, and 1 capsule formulation (C) with a total of 3 oral formulations: AUC and Cmax Total number of animals required: 16
Basic Design:
Cross-over design, 8 animals per arm:

TABLE 12a

| Period 1 (single dose of capsule, day 1): | | | | | |
|---|---|---|---|---|---|
| Group | Treatment | Dose | Dose (mg) | # Number of animals | Animal numbers |
| 1 | Bendamustine | Capsule | 50 | 4 Male + 4 Female | |
| 2 | Bendamustine | Capsule | 50 | 4 Male + 4 Female | |

One Week Wash-Out

TABLE 12b

| Period 2 (1 week after period 1, single dose of either of the following formulations, day 8): | | | | | |
|---|---|---|---|---|---|
| Group | Treatment | Dose route | Dose (mg) | # Number of animals | Animal numbers |
| 1 | Bendamustine | Formulation X | 50 | 4 Male + 4 Female | |
| 2 | Bendamustine | T4 | 50 | 4 Male + 4 Female | |

Example 11

The coated tablets of Example 9 (formulation 3, coated with Opadry® Tablets T4), containing 50 mg of bendamustine, were orally administered to male and female dogs in comparison with the capsules of the reference example.

The mean plasma profiles vs. time for both the capsule formulation and the coated tablet of Example 9 are shown in FIG. 1.

Example 12

The coated tablets of Examples 6, 7, or 8 (Tablets T1 to T3), containing 50 mg of bendamustine, were orally administered to male and female dogs in comparison with the capsules of the reference example.

The mean plasma profiles vs. time of the capsule formulation and the coated tablets of Examples 6 to 8 are shown in FIG. 1.

Experiments were conducted in order to:
assess which saccharides or saccharide mixtures are suitable to obtain chemically stable tablets, with fast dissolution profile and hardness values suitable for coating;
evaluate the compatibility between API and excipients;
develop placebo and API-containing batches by investigating different manufacturing processes: dry granulation, direct compression and wet granulation;
evaluate different bendamustine hydrochloride/saccharide weight ratios;
evaluate the impact of saccharide purity on the formation of bendamustine hydrochloride purities;

investigate the influence of moisture content on the technological properties and stability of the manufactured tablets;

manufacture tablets using the commercially available freeze dried bendamustine hydrochloride product (Ribomustin®) and to compare the properties of these tablets with tablets produced using corresponding amounts of mannitol and bendamustine hydrochloride.

The following saccharidests were used for the manufacturing of tablets in accordance with the invention, the tablets containing 50 mg of bendamustine (55 mg as bendamustine hydrochloride)

TABLE 13

| Chemical name | Product name/ Manufacturer | Class |
|---|---|---|
| Dextrose anhydrous | Dextrose anhydrous C/Roquette | Monosaccharide |
| Dextrose anhydrous | Dextrose anhydrous ST 0.5/Roquette | Monosaccharide |
| Dextrose monohydrate | Dextrose monohydrate G/Roquette | Monosaccharide |
| Dextrose monohydrate | Dextrose monohydrate M/Roquette | Monosaccharide |
| Lactitol monohydrate | Lacty-M/Purac Biochem Lactitol MC/Danisco | Disaccharide |
| Trehalose | Treha 16400/Cargill | Disaccharide |
| Sorbitol | Neosorb P60W/Roquette | Monosaccharide |
| Erythritol | Zerose (TM) Erythritol 16954/Cargill | Monosaccharide |
| Maltose Monohydrate | Sunmalt S/Hayashibara | Disaccharide |
| Mannitol | Pearlitol 200 SD/Roquette | Monosaccharide |
| Lactose anhydrous | SuperTab 21 AN/DMV-Fonterra Excipients | Disaccharide |
| Lactose monohydrate | SuperTab 14 SD/DMV-Fonterra Excipients | Disaccharide |
| Fructose | Fructose MS/Galam | Monosaccharide |
| Maltitol | Sweetpearl P200/Roquette | Disaccharide |
| Xylitol | Xylisorb 300/Roquette | Monosaccharide |
| Sucrose | Sucrose Comprizucker S/Suedzucker | Disaccharide |
| Sucrose | Sucrose RFS/Suedzucker | Disaccharide |
| Sucrose 97% + Maltodextrin 3% | EV saccharide DC 3, 75 MD/Vibar Nord SPA | Disaccharide |
| β-Cyclodextrin | Kleptose DC/Roquette | Cyclic eptasaccharide |
| D-Raffinose Pentahydrate | n/a/Senn Chemicals | Trisaccharide |
| D-Melezitose monohydrate | n/a/Biosynth | Trisaccharide |
| Microcrystalline Cellulose | Avicel PH112/FMC Biopolymer | Polysaccharide |
| Microcrystalline Cellulose | Avicel pH101/FMC Biopolymer | Polysaccharide |

The quality of the batches made was assessed by observation of the physical appearance, identification test (HPLC), dissolution test, content and related substances assay (HPLC), content uniformity test(HPLC), hardness test and water content (Karl Fischer method). Batches were submitted to accelerated stability studies packaged in amber glass bottles under the storage conditions detailed in the following table. For each manufactured API-containing batch some tablets were stored at 5° C. as back-up samples.

In the following, the various excipients in relation to their manufacturing process were investigated. By using these excipients several placebo manufacturing trials were carried out by dry granulation to obtain preliminary information about the manufacturing method suitable to obtain tablets with good quality.

Two types of disintegrants were used: microcrystalline cellulose (Avicel® PH 112), as a standard disintegrant, and cross-linked polyvinylpyrrolidone (Crospovidone®), used just for batch D001T/002. The choice of Crospovidone® for batch D001T/002 (filler: anhydrous lactose) was based on the similarity between this formulation and the prototype formulation of example 9. Magnesium stearate was used as lubricant for all the batches produced. The dry granulation manufacturing process for placebo trials consisted in the following steps:

1. The saccharide and a partial quantity of lubricant (83.3%$_{w/w}$ of the total amount) were accurately weighed and then mixed in a polyethylene bag for 2 minutes.
2. The obtained mixture was compacted by using the tabletting machine equipped with a 18 mm diameter punch.
3. The obtained slugs were sieved by using a 850 micron net.
4. The granulate was weighed and mixed with the disintegrant and the remaining amount of the lubricant (16.7%$_{w/w}$) in a polyethylene bag for 2 minutes and then tabletted by using a 10 mm diameter punch.

Table 14 and Table 15 summarize the composition of each Placebo formulation and the results of the analytical tests performed on both the final mixtures and the tablets. In Table 16, observations made during the manufacturing process of placebo batches and/or during their analytical characterization are reported.

The analytical and physical test results carried out on placebo batches D001T/001-D001T/002-D001T/004-D001T/013-D001T/015 showed that these formulations are suitable to be manufactured by dry granulation and further investigated by the addition of the API. All the other formulations are characterized by a powder difficult to compact and, when obtained, tablets with high friability.

Batch D001 T/005 (filler: β-cyclodextrin) showed good behaviour in dry manufacturing process, high hardness, low friability but long disintegration time. This formulation was further investigated by employing a super disintegrant (Crospovidone®) and adding the API (see following paragraph).

TABLE 14

Dry granulation-Placebo batches composition and analytical results (batches D001T/001 ÷ D001T/010).

| Components | Placebo Batches manufactured by Dry Granulation | | | | | | | | | |
|---|---|---|---|---|---|---|---|---|---|---|
| | D001T/001 (%$_{w/w}$) | D001T/002 (%$_{w/w}$) | D001T/003 (%$_{w/w}$) | D001T/004 (%$_{w/w}$) | D001T/005 (%$_{w/w}$) | D001T/006 (%$_{w/w}$) | D001T/007 (%$_{w/w}$) | D001T/008 (%$_{w/w}$) | D001T/009 (%$_{w/w}$) | D001T/010 (%$_{w/w}$) |
| Lactose Monohydrate (SuperTab 14 SD) | 93.7 | — | — | — | — | — | — | — | — | — |
| Lactose Anhydrous (SuperTab 21 AN) | — | 93.7 | — | — | — | — | — | — | — | — |

TABLE 14-continued

Dry granulation-Placebo batches composition and analytical results (batches D001T/001 ÷ D001T/010).

Placebo Batches manufactured by Dry Granulation

| Components | D001T/001 (%w/w) | D001T/002 (%w/w) | D001T/003 (%w/w) | D001T/004 (%w/w) | D001T/005 (%w/w) | D001T/006 (%w/w) | D001T/007 (%w/w) | D001T/008 (%w/w) | D001T/009 (%w/w) | D001T/010 (%w/w) |
|---|---|---|---|---|---|---|---|---|---|---|
| Mannitol (Pearlitol 200 SD) | — | — | 93.7 | — | — | — | — | — | — | — |
| Sorbitol (Neosorb P60W) | — | — | — | 93.7 | — | — | — | — | — | — |
| β-Cyclodextrin (Kleptose DC) | — | — | — | — | 93.7 | — | — | — | — | — |
| Dextrose Anhydrous (Dextrose Anhydrous C) | — | — | — | — | — | 93.7 | — | — | — | — |
| Dextrose Monohydrate (Dextrose Monohydrate G) | — | — | — | — | — | — | 93.7 | — | — | — |
| D-Raffinose Pentahydrate | — | — | — | — | — | — | — | 93.7 | — | — |
| Trehalose (Treha 16400) | — | — | — | — | — | — | — | — | 93.7 | — |
| Erythritol (Zerose Erythritol 16954) | — | — | — | — | — | — | — | — | — | 99.5 |
| Avicel PH 112 | 5.7 | — | 5.7 | 5.7 | 5.7 | 5.7 | 5.7 | 5.7 | 5.7 | — |
| Crospovidone | — | 5.7 | — | — | — | — | — | — | — | — |
| Magnesium Stearate | 0.6 | 0.6 | 0.6 | 0.6 | 0.6 | 0.6 | 0.6 | 0.6 | 0.6 | 0.5 |
| Results of analytical tests performed on final mixtures ||||||||||| |
| Water Content (%) | 5.26 | 0.85 | 0.47 | 0.93 | 12.62 | 0.47 | 8.47 | 14.59 | 9.36 | N.A. |
| Flowability (seconds) (Test performed according to EP 6.0, par. 2.9.16) | 24.68 (Nozzle 1, diameter = 10.0 mm) | 4.66 (Nozzle 3, diameter = 25.0 mm) | 9.91 (Nozzle 2, diameter = 15.0 mm) | 13.70 (Nozzle 1, diameter = 10.0 mm) | 15.61 (Nozzle 1, diameter = 10.0 mm) | 27.70 (Nozzle 1, diameter = 10.0 mm) | 25.37 (Nozzle 1, diameter = 10.0 mm) | 19.43 (Nozzle 1, diameter = 10.0 mm) | 20.85 (Nozzle 1, diameter = 10.0 mm) | N.A. |
| Results of analytical tests performed on tablets ||||||||||| |
| Hardness (N) | 70 | 99 | 86 | 148 | 127 | N.A. | 54 | 46 | 61 | N.A. |
| Friability (%) (Test performed according to EP 6.0, par. 2.9.7) | 0.1 | 0.1 | 0.6 | 0.2 | 0.2 | N.A. | Test failure (39.4) | Test failure (31.7) | Test failure (44.9) | N.A. |
| Mean Weight (mg/tablet) | 360 | 365 | 319 | 332 | 327 | N.A | 365 | 337 | 335 | N.A. |
| Disintegration (min · sec) (medium: buffer pH = 1.5) | 5'07" | 1'24" | 2'51" | 4'56" | 20'59" | N.A. | 4'18" | 1'22" | 3'59" | N.A. |

N.A. = not available because the mixture is not suitable for tabletting process (see the observations reported in table 5a)

TABLE 15

Dry granulation-Placebo batches composition and analytical results (batches D001T/011 ÷ D001T/025).

Placebo Batches manufactured by Dry Granulation

| Components | D001T/011 (%w/w) | D001T/012 (%w/w) | D001T/013 (%w/w) | D001T/014 (%w/w) | D001T/015 (%w/w) | D001T/016 (%w/w) | D001T/017 (%w/w) | D001T/018 (%w/w) | D001T/019 (%w/w) | D001T/025 (%w/w) |
|---|---|---|---|---|---|---|---|---|---|---|
| Fructose (Fructose MS) | 93.7 | — | — | — | — | — | — | — | — | — |
| Maltitol (Sweetpearl P200) | — | 93.7 | — | — | — | — | — | — | — | — |
| Maltose Monohydrate (Sunmalt S) | — | — | 93.7 | — | — | — | — | — | — | — |
| Lactitol Monohydrate (Lacty M) | — | — | — | 93.7 | — | — | — | — | — | — |
| Sucrose 97% + Maltodextrin 3% (EV Saccharide DC 3.75 MD) | — | — | — | — | 93.7 | — | — | — | — | — |
| Sucrose (Sucrose Comprizucker S) | — | — | — | — | — | 99.5 | — | — | — | — |
| Sucrose (Sucrose granular RFS) | — | — | — | — | — | — | 93.7 | — | — | — |
| Xylitol (Xylisorb 300) | — | — | — | — | — | — | — | 99.5 | — | — |
| β-Cyclodextrin (Kleptose DC) | — | — | — | — | — | — | — | — | 93.8 | — |
| D-Melezitose monohydrate | — | — | — | — | — | — | — | — | — | 93.8 |
| Avicel PH 112 | — | 5.7 | 5.7 | 5.7 | 5.7 | — | 5.7 | — | — | — |
| Crospovidone | 5.7 | — | — | — | — | — | — | — | 5.6 | 5.6 |
| Magnesium Stearate | 0.6 | 0.6 | 0.6 | 0.6 | 0.6 | 0.5 | 0.6 | 0.5 | 0.6 | 0.6 |

TABLE 15-continued

Dry granulation-Placebo batches composition and analytical results (batches D001T/011 ÷ D001T/025).

Placebo Batches manufactured by Dry Granulation

| Components | D001T/011 (%w/w) | D001T/012 (%w/w) | D001T/013 (%w/w) | D001T/014 (%w/w) | D001T/015 (%w/w) | D001T/016 (%w/w) | D001T/017 (%w/w) | D001T/018 (%w/w) | D001T/019 (%w/w) | D001T/025 (%w/w) |
|---|---|---|---|---|---|---|---|---|---|---|
| *Results of analytical tests performed on final mixtures* | | | | | | | | | | |
| Water Content (%) | 0.42 | 0.38 | 5.71 | 5.45 | 0.78 | N/A | 0.32 | N/A | 12.30 | |
| Flowability (seconds) (Test performed according to EP 6.0, par. 2.9.16) | 19.09 (Nozzle 1, diameter = 10.0 mm) | 22.54 (Nozzle 1, diameter = 10.0 mm) | 16.57 (Nozzle 1, diameter = 10.0 mm) | 23.41 (Nozzle 1, diameter = 10.0 mm) | 5.37 (Nozzle 3, diameter = 25.0 mm) | N/A | 17.38 (Nozzle 1, diameter = 10.0 mm) | N/A | 18.64 (Nozzle 1, diameter = 10.0 mm) | Not flow (Nozzle 3, diameter = 25.0 mm) |
| *Results of analytical tests performed on tablets* | | | | | | | | | | |
| Hardness (N) | 17 | 33 | 130 | 69 | 69 | N/A | 19 | N/A | 62 | 56 |
| Friability (%) (Test performed according to EP 6.0, par. 2.9.7) | Test failure (100.0) | Test failure (100.0) | 0.2 | Test failure (19.6) | 0.4 | N/A | Test failure (78.0) | N/A | 0.2 | Test failure (20.7) |
| Mean Weight (mg/tablet) | 380 | 388 | 328 | 338 | 349 | N/A | 383 | N/A | 338 | 328 |
| Disintegration (min.) (medium: buffer pH = 1.5) | 5'52" | 6'40" | 5'09" | 6'32" | 5'47" | N/A | 4'50" | N/A | 4'01" | 3'30" |

N/A = not available because the mixture is not suitable for tabletting process (see the observations reported in table 5a)

TABLE 16

Observations about manufacturing process, product technological properties and analytical tests for each manufactured placebo batch

| Placebo Batches | Dry Granulation process/ obtained slugs | Tabletting Process/ obtained tablets | Analytical tests on tablets |
|---|---|---|---|
| D001T/001 | Excellent slugs; easy to be sieved | Easy to be tabletted; good tablets obtained | Fast disintegration; low friability; medium hardness |
| D001T/002 | Good slugs; easy to be sieved | Easy to be tabletted; good tablets obtained | Fast disintegration; low friability; high hardness |
| D001T/003 | Difficult to compact; high pressure needed to obtain slugs | Difficult to be tabletted; The powder adheres to punches; tabletting process was interrupted after a few tablets | Fast disintegration; high friability; high hardness |
| D001T/004 | Excellent slugs; easy to be sieved | Fairly good to be tabletted; good tablets obtained | Fast disintegration; low friability; very high hardness |
| D001T/005 | Excellent slugs; easy to be sieved | Easy to be tabletted; good tablets obtained | Slow disintegration; low friability; high hardness |
| D001T/006 | Poor slugs, high friability | Impossible to be tabletted; tabletting process interrupted | No tablets available for analytical testing |
| D001T/007 | Poor slugs, high friability | Good to be tabletted; fairly good tablets obtained | Fast disintegration; very high friability, above acceptance limit; medium hardness |
| D001T/008 | Poor slugs, high friability | Good to be tabletted; fairly good tablets obtained | Fast disintegration; very high friability, above acceptance limit; medium hardness |
| D001T/009 | Good slugs; easy to be sieved | Good to be tabletted; fairly good tablets obtained | Fast disintegration; very high friability, above acceptance limit; medium hardness |
| D001T/010 | Impossible to obtain slugs; not further processed | — | — |
| D001T/011 | Poor slugs, high friability | Poor tablets obtained (many tablets break during tabletting process) | Fast disintegration; very high friability, above acceptance limit (all tablets broken after test); very low hardness |
| D001T/012 | Poor slugs, high friability | Poor tablets obtained (many tablets break during tabletting process) | Fast disintegration; very high friability, above acceptance limit (all tablets broken after test); low hardness |
| D001T/013 | Excellent slugs; easy to be sieved | Easy to be tabletted; good tablets obtained | Fast disintegration; low friability; very high hardness |
| D001T/014 | Good slugs; easy to be sieved | Good to be tabletted; fairly good tablets obtained | Fast disintegration; high friability, above acceptance limit; medium hardness |
| D001T/015 | Good slugs; easy to be sieved | Good to be tabletted; good tablets obtained | Fast disintegration; medium friability; medium hardness |
| D001T/016 | Impossible to obtain slugs; not further processed | — | — |
| D001T/017 | Poor slugs, high friability | Poor tablets obtained (many tablets break during tabletting process) | Fast disintegration; high friability, above acceptance limit; low hardness |
| D001T/018 | Impossible to obtain slugs; not further processed | — | — |
| D001T/019 | Excellent slugs; easy to be sieved | Easy to be tabletted; good tablets obtained | Fast disintegration; low friability; medium hardness |
| D001T/025 | Good slugs; easy to be sieved | Good to be tabletted; fairly good tablets obtained | Fast disintegration; very high friability, above acceptance limit; medium hardness |

Batches Manufactured by Dry Granulation with a 1:5 Bendamustine Hydrochloride/Saccharide Weight Ratio The placebo formulations, evaluated as more suitable to manufacture tablets containing the active pharmaceutical ingredient (API) by dry granulation, were modified to include the API and two API/saccharide weight ratios were explored: 1:5 and 1:2.

In this paragraph, formulations with a 1:5 API/saccharide weight ratios are described.

Two types of disintegrant were used: microcrystalline cellulose (Avicel® PH 112), as a standard disintegrant, and crosslinked polyvivylpyrrolidone (Crospovidone), used just for the batch D001T/022. Magnesium stearate was used as lubricant for all the batches produced.

The manufacturing process of the API-containing batches by dry granulation consisted in the following steps:
1. The saccharide, a partial quantity of lubricant (83.3%$_{w/w}$ of the total amount) and Bendamustine Hydrochloride were accurately weighed and mixed in a double polyethylene bag for 5 minutes.
2. The powder blend was pressed by using the tabletting machine equipped with 18 mm diameter punch.
3. To obtain a granulate, the produced slugs were sieved by using a 850 micron net.
4. The granulate was weighed and mixed with the disintegrant and the remaining amount of the lubricant (16.7%$_{w/w}$) in a double polyethylene bag for 5 minutes.
5. The obtained mixture was tabletted by using a 10 mm diameter punch.

Table 17 summarizes the composition of each API-containing formulation manufactured and the results of the analytical tests performed on the API-containing final mixtures; table 18 summarizes the results of the analytical tests performed on the obtained products.

TABLE 17

Dry granulation - API/Saccharide weight ratio 1:5. API-containing batches final mixture composition and analytical results.

| Components | API-containing batches manufactured by Dry granulation API/Saccharide ratio 1:5 | | | | |
|---|---|---|---|---|---|
| | D001T/020 (%$_{w/w}$) | D001T/021 (%$_{w/w}$) | D001T/022 (%$_{w/w}$) | D001T/023 (%$_{w/w}$) | D001T/024 (%$_{w/w}$) |
| Bendamustine HCL | 15.3 | 16.6 | 16.6 | 16.6 | 15.7 |
| Lactose Monohydrate (SuperTab 14 SD) | 78.4 | — | — | — | — |
| Sorbitol (Neosorb P60W) | — | 77.1 | — | — | — |
| β-Cyclodextrin (Kleptose DC) | — | — | 77.1 | — | — |
| Maltose (Food grade) (Sunmalt S) | — | — | — | 77.1 | — |
| Sucrose 97% + Maltodextrin 3%) (EV Saccharide DC 3.75 MD) | — | — | — | — | 78.0 |
| Avicel PH 112 | 5.7 | 5.7 | — | 5.7 | 5.7 |
| Crospovidone | — | — | 5.7 | — | — |
| Magnesium Stearate | 0.6 | 0.6 | 0.6 | 0.6 | 0.6 |
| | Result of analytical tests performed on final mixture | | | | |
| Flowability (seconds) (Test performed according to EP 6.0, par. 2.9.16) | 7.31 (Nozzle 2, diameter = 15 mm) | 19.91 (Nozzle 1, diameter = 10 mm) | 3.89 (Nozzle 3, diameter = 25 mm) | 23.00 (Nozzle 1, diameter = 10 mm) | 7.99 (Nozzle 3, diameter = 25 mm) |

TABLE 18

Dry granulation-API//Saccharide weight ratio 1:5. API-containing batches tablets analytical results.

| Analytical Test | Specification Limits | Results of analytical tests performed on tablets | | | | |
|---|---|---|---|---|---|---|
| | | D001T/020 | D001T/021 | D001T/022 | D001T/023 | D001T/024 |
| Identification (HPLC) | Positive | Positive | Positive | Positive | Positive | Positive |
| Mean Weight (mg/tablet) | Specific for each formulation | 359.43 Limits: 342 + 378 | 336.27 Limits: 315.4 + 348.6 | 334.67 Limits: 315.44 + 348.6 | 333.19 Limits: 315.4 + 348.6 | 349.72 Limits: 332.5 + 367.5 |
| Content Uniformity (Test performed according to EP 6.0) | Complies | Complies RSD 1.26 | Complies RSD 1.42 | Complies RSD 0.84 | Complies RSD 0.58 | Complies RSD 2.02 |

TABLE 18-continued

Dry granulation-API//Saccharide weight ratio 1:5. API-containing batches tablets analytical results.

| Analytical Test | Specification Limits | Results of analytical tests performed on tablets | | | | |
|---|---|---|---|---|---|---|
| | | D001T/020 | D001T/021 | D001T/022 | D001T/023 | D001T/024 |
| Assay (%) (HPLC) | 95.0%-105.0% | 96.9 | 93.5 | 97.4 | 93.8 | 97.7 |
| Related substances (%) (HPLC) | | | | | | |
| HP1 | ≤0.5% | 0.12 | 0.10 | 0.08 | 0.11 | 0.14 |
| BM1 Dimer | ≤0.2% | 0.04 | 0.05 | 0.05 | 0.05 | 0.04 |
| BM1EE | ≤0.5% | 0.14 | 0.13 | 0.13 | 0.13 | 0.15 |
| NP1 | ≤0.2% | n.d. | n.d. | 0.01 | n.d. | 0.1 |
| Individual unknown impurity | ≤0.1% | 0.01 | n.d. | n.d. | n.d. | n.d. |
| Total impurities | ≤1.5% | 0.31 | 0.28 | 0.27 | 0.29 | 0.34 |
| Dissolution Test (Medium: buffer pH = 1.5) | | | | | | |
| (%10 min) | 80% in 30 minutes | 72.9 | 72.1 | 88.0 | 60.0 | 75.5 |
| (%20 min) | | 87.6 | 85.9 | 88.9 | 79.2 | 89.6 |
| (%30 min) | | 87.2 | 84.7 | 87.4 | 84.7 | 90.3 |
| Moisture content (%) | — | 4.72 | 1.00 | 11.3 | 5.13 | 0.88 |
| Hardness (N) | ≥40 N | 67 | 89 | 77 | 151 | 55 |
| Friability (%) (Test performed according to EP 6.0, par. 2.9.7) | ≤1.0% | 0.2 | 0.2 | 0.1 | 0.2 | 0.4 |

The results of analytical tests performed both on final mixtures and finished products were in most cases good, mainly for Content Uniformity and Purity. All API-containing batches showed satisfactory mass uniformity, homogeneity of API content, and a low impurities content. The impurity profile of all formulations was in compliance with the specifications of API (see specification limits in the tables), thus no degradation occurs during manufacturing process.

Two API-containing batches showed low values in API assay; this result could be due to the small batch size and to the losses during the manufacturing process and the samples for IPCs on the final mixtures.

API-Containing Batches Manufactured by Dry Granulation with a 1:2 API/Saccharide Weight Ratio All the saccharide previously investigated by thy granulation to manufacture tablets with a 1:5 API/Saccharide weight ratio were also evaluated at a ratio of 1:2.

For the manufacturing process see above. In this case, the obtained mixture was tabletted by using a 8 mm diameter punch.

Two types of disintegrant were used: microcrystalline cellulose (Avicel® PH 112), as a standard disintegrant, and crosslinked polyvinylpyrrolidone (Ccrospovidone®', used just for the batch D001T/105. For this batch we have explored the use of Avicel® PH 112 and of Crospovidone®. The Crospovidone® was chosen according to the previous cyclodextrin based formulation manufactured by dry granulation with a 1:5 API/Saccharide (see previous results).

Table 19 and Table 20 summarize the composition of each API-containing formulation manufactured by dry granulation with an API/Saccharide weight ratio of 1:2 and the results of the analytical tests performed on both, the final mixtures and the tablets. All API-containing batches showed suitable uniformity of mass, homogeneity of API content and low impurities content. Friability and hardness values are, in the most of the cases, in compliance with the specifications. In the case of batches D001 T/093, D001T/095 and D001T/096, the results of the dissolution test performed on 6 tablets showed out of specifications values with a high RSD and the test was extended to a sample of 12 tablets.

Cyclodextrin based tablets show good properties with both disintegrants (Avicel® PH 112 and Crospovidone®).

TABLE 19

Dry granulation-API/Saccharide weight ratio 1:2. API-containing batches final mixture composition and analytical results.

| | API-containing Batches manufactured by Dry Granulation API/SaccharideSaccharide ratio 1:2 | | | | | | |
|---|---|---|---|---|---|---|---|
| Components | D001T/091 (%$_{w/w}$) | D001T/092 (%$_{w/w}$) | D001T/093 (%$_{w/w}$) | D001T/094 (%$_{w/w}$) | D001T/105 (%$_{w/w}$) | D001T/095 (%$_{w/w}$) | D001T/096 (%$_{w/w}$) |
| Bendamustine HCl | 31.1 | 31.1 | 31.1 | 31.1 | 31.1 | 31.1 | 31.1 |
| Lactose Monohydrate (Supertab 14 SD) | 62.3 | — | — | — | — | — | — |
| Lactose Anhydrous (Supertab 21 AN) | — | 62.3 | — | — | — | — | — |
| Sorbitol (Neosorb P60W) | — | — | 62.3 | — | — | — | — |

TABLE 19-continued

Dry granulation-API/Saccharide weight ratio 1:2. API-containing batches final mixture composition and analytical results.

API-containing Batches manufactured by Dry Granulation API/SaccharideSaccharide ratio 1:2

| Components | D001T/091 (%w/w) | D001T/092 (%w/w) | D001T/093 (%w/w) | D001T/094 (%w/w) | D001T/105 (%w/w) | D001T/095 (%w/w) | D001T/096 (%w/w) |
|---|---|---|---|---|---|---|---|
| β-Ciclodextrine (Kleptose DC) | — | — | — | 62.3 | 62.3 | — | — |
| Sucrose 97% + Maltodextrine 3% (EV SaccharideSaccharide DC 3.75 MD) | — | — | — | — | — | 62.3 | — |
| Maltose (Food grade) (Sunmalt S) | — | — | — | — | — | — | 62.3 |
| Avicel PH 112 | 5.9 | 5.9 | 5.9 | 5.9 | | 5.9 | 5.9 |
| Crospovidone | | | | | 5.9 | | |
| Magnesium Stearate | 0.7 | 0.7 | 0.7 | 0.7 | 0.7 | 0.7 | 0.7 |
| Results of analytical tests performed on final mixtures | | | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) |

TABLE 20

Dry granulation-API/Saccharide weight ratio 1:2. API-containing batches tablets analytical results.

| Analytical Test | Specification Limits | D001T/091 | D001T/092 | D001T/093 | D001T/094 | D001T/105 | D001T/095 | D001T/096 |
|---|---|---|---|---|---|---|---|---|
| Identification (HPLC) | Positive | Positive | Positive | Positive | Positive | Positive | Positive | Positive |
| Mean Weight (mg/tablet) | Specific for each formulation | 175.01 Limits: 168.2 + 185.9 | 178.85 Limits: 168.2 + 185.9 | 176.90 RSD 2.3 Limits: 168.2 + 185.9 | 176.06 Limits: 168.2 + 185.9 | 176.40 Limits: 168.2 + 185.9 | 175.81 RSD 6.1 Limits: 168.2 + 185.9 | 180.81 RSD 1.3 Limits: 168.2 + 18.9 |
| Content Uniformity (Test performed according to EP 6.0) | Complies | Complies RSD 2.43. | Complies RSD 2.41 | Complies RSD 3.34 | Complies RSD 3.84 | Complies RSD 2.69 | Complies RSD 2.86 | Complies RSD 3.41 |
| Assay (%) (HPLC) | 95.0%-105.0% | 96.0 | 96.8 | 96.6 | 96.6 | 97.2 | 97.7 | 99.3 |
| Related substances (%) (HPLC) | | | | | | | | |
| HP1 | ≤0.50% | 0.08 | 0.28 | 0.11 | 0.11 | 0.19 | 0.12 | 0.08 |
| BM1 Dimer | ≤0.20% | 0.04 | 0.03 | 0.04 | 0.04 | 0.05 | 0.04 | 0.04 |
| BM1EE | ≤0.50% | 0.13 | 0.13 | 0.13 | 0.14 | 0.13 | 0.12 | 0.13 |
| NP1 | ≤0.20% | 0.01 | 0.01 | 0.01 | 0.01 | 0.01 | 0.01 | 0.02 |
| Individual unknown impurity | ≤0.10% | n.d. | 0.04 | 0.06 | 0.05 | 0.02 | 0.05 | 0.03 |
| Total impurities | ≤1.50% | 0.27 | 0.54 | 0.36 | 0.35 | 0.40 | 0.37 | 0.31 |
| Total impurities after storage at 40° C./75% RH for 3 months | | 0.29 | 0.31 | 0.31 | 0.32 | | 0.35 | 0.35 |
| Dissolution Test (Medium: buffer pH = 1.5) | | | | n = 12 | | | n = 12 | n = 12 |
| (%10 min) | 80% in 30 min | 49.2 | 84.7 | 36.2 (RSD 15.7) | 68.8 | 75.0 | 58.2 (RSD 24.3) | 57.5 (RSD 22.2) |
| (%20 min) | | 75.2 | 92.4 | 54.6 (RSD 14.0) | 88.8 | 92.1 | 73.8 (RSD 19.1) | 75.1 (RSD 17.5) |
| (%30 min) | | 84.7 | 93.0 | 65.2 (RSD 10.4) | 92.4 | 92.8 | 82.5 (RSD 20.5) | 84.6 (RSD 19.7) |
| Dissolution after storage at 40° C./75% RH for 3 months | | 89 | 92 | 86 | 92 | | 75 | 89 |
| Moisture content (%) | — | 4.02 | 0.62 | 0.70 | 8.30 | 8.70 | 0.71 | 4.06 |

TABLE 20-continued

Dry granulation-API/Saccharide weight ratio 1:2. API-containing batches tablets analytical results.

| Analytical Test | Specification Limits | Results of analytical tests performed on tablets | | | | | | |
|---|---|---|---|---|---|---|---|---|
| | | D001T/091 | D001T/092 | D001T/093 | D001T/094 | D001T/105 | D001T/095 | D001T/096 |
| Hardness (N) | ≥40 N | 95 | 49 | 118 | 110 | 100 | 75 | 125 |
| Friability (%) (Test performed according to EP 6.0) | ≤1.0% | 0.5 | 0.7 | 0.3 | 0.5 | 0.5 | 1.5 | 0.1 | n.d. = not detected

API-Containing Batches Manufactured by Direct Compression with a 1:5 API/Saccharide Saccharide Weight Ratio The saccharides with suitable characteristics to be manufactured by dry granulation were also explored by using direct compression developing tablets with a 1:5 API/Saccharide ratio.

Two types of disintegrant were used: microcrystalline cellulose (Avicel® PH 112), as a standard disintegrant, and crosslinked polyvinylpyrrolidone (Crospovidone®), used just for batch D001T/029.

This manufacturing process consisted of the following steps:

1. Weighing the API and the excipients.
2. Transferring the raw materials in a double polyethylene bag and mixing for about 5 minutes until an homogeneous powder blend is obtained.
3. Transferring of the powder blend in the hopper of the tabletting machine.
4. Compression of the powder blend using an eccentric tablet machine equipped with a 10 mm diameter punch.

The characteristics of the API-containing batches manufactured by direct compression are presented in the following table.

TABLE 21

Direct Compression - API/Saccharide weight ratio 1:5. API-containing batches final mixture composition and analytical results.

| | API-containing batches manufactured by Direct Compression | | | | |
|---|---|---|---|---|---|
| | D001T/026 (%$_{w/w}$) | D001T/027 (%$_{w/w}$) | D001T/028 (%$_{w/w}$) | D001T/029 (%$_{w/w}$) | D001T/030 (%$_{w/w}$) |
| Bendamustine HCL | 16.6 | 16.6 | 15.3 | 16.6 | 15.7 |
| Lactose Monohydrate (Supertab 14 SD) | — | — | 78.4 | — | — |
| Sorbitol (Neosorb P60W) | — | 77.1 | — | — | — |
| β-Cyclodextrin (Kleptose DC) | — | — | — | 77.1 | — |
| Maltose (Food grade) (Sunmalt S) | 77.1 | — | — | — | — |
| Sucrose 97% + Maltodextrin 3% (EV Saccharide DC 3.75 MD) | — | — | — | — | 78.0 |
| Avicel PH 112 | 5.7 | 5.7 | 5.7 | — | 5.7 |
| Crospovidone | — | — | — | 5.7 | — |
| Magnesium Stearate | 0.6 | 0.6 | 0.6 | 0.6 | 0.6 |
| Flowability (seconds) (Test performed according to EP 6.0, par. 2.9.16) | 4.78 (Nozzle 3, diameter = 25 mm) | 4.01 (Nozzle 3, diameter = 25 mm) | Not flow (Nozzle 3, diameter = 25 mm) | Not flow (Nozzle 3, diameter = 25 mm) | 4.12 (Nozzle 3, diameter = 25 mm) |

The obtained results of the analytical tests are listed in table 22.

TABLE 22

Direct Compression-API/Saccharide weight ratio 1:5. API-containing batches tablets analytical results.

| Analytical Test | Specification Limits | Result of analytical Tests performed on tablets | | | | |
|---|---|---|---|---|---|---|
| | | D001T/026 | D001T/027 | D001T/028 | D001T/029 | D001T/030 |
| Identification (HPLC) | Positive | Positive | Positive | Positive | Positive | Positive |
| Mean Weight (mg/tablet) | Specific for each Limits: | 333.80 Limits: | 332.25 Limits: | 363.86 Limits: | 331.41 Limits: | 356.61 Limits: |

TABLE 22-continued

Direct Compression-API/Saccharide weight ratio 1:5. API-containing batches tablets analytical results.

|  | Specification | Result of analytical Tests performed on tablets | | | | |
|---|---|---|---|---|---|---|
| Analytical Test | Limits | D001T/026 | D001T/027 | D001T/028 | D001T/029 | D001T/030 |
|  | formulation | 315.4 + 348.6 | 315.4 + 348.6 | 342.0 + 378.0 | 315.4 + 348.6 | 332.5 + 367.5 |
| Content Uniformity (Test performed according to EP 6.0) | Complies | Complies RSD 3.51 | Complies RSD 3.60 | Complies RSD 0.88 | Complies RSD 1.57 | Not Complies RSD 10.84 |
| Assay (%) (HPLC) | 95.0%-105.0% | 94.5 | 97.2 | 100.8 | 100.1 | 99.6 |
| Related substances (%) (HPLC) | | | | | | |
| HP1 | ≤0.5% | 0.10 | 0.11 | 0.12 | 0.13 | 0.11 |
| BM1 Dimer | ≤0.2% | 0.04 | 0.04 | 0.04 | 0.04 | 0.04 |
| BM1EE | ≤0.5% | 0.13 | 0.15 | 0.14 | 0.14 | 0.14 |
| NP1 | ≤0.2% | 0.01 | 0.01 | 0.02 | 0.01 | 0.02 |
| Individual unknown impurity | ≤0.1% | 0.03 | 0.03 | 0.03 | 0.03 | 0.03 |
| Total impurities | ≤1.5% | 0.31 | 0.34 | 0.35 | 0.35 | 0.34 |
| Dissolution Test (Medium: buffer pH = 1.5) | | | | | | |
| (%10 min) | 80% in 30 minutes | 45.5 | 71.5 | 54.7 | 83.3 | 73.5 |
| (%20 min) | | 69.7 | 89.7 | 88.6 | 89.5 | 90.9 |
| (%30 min) | | 83.3 | 89.3 | 91.1 | 91.5 | 91.3 |
| Moisture content (%) | — | 5.04 | 0.71 | 4.40 | 11.26 | 0.83 |
| Hardness (N) | ≥40 N | 106 | 108 | 74 | 99 | 92 |
| Friability (%) (Test performed according to EP 6.0, par. 2.9.7) | ≤1.0% | 0.2 | 0.2 | 0.2 | 0.1 | 0.8 |

As reported in the above table the API-containing tablets manufactured by direct compression showed no critical differences from the ones produced by dry granulation except for batch D001T/030 (filler: Sucrose 97%+Maltodextrin 3%) that showed a non homogeneous API content and a slight increase in the value of friability.

Wet Granulation:
Placebo Exploratory Trials

Based on the results obtained in the first and second part of the project, the saccharides not suitable for dry granulation or direct compression were investigated by wet granulation.

The present approach to investigate the wet granulation technology is shown below.

Figure 2:
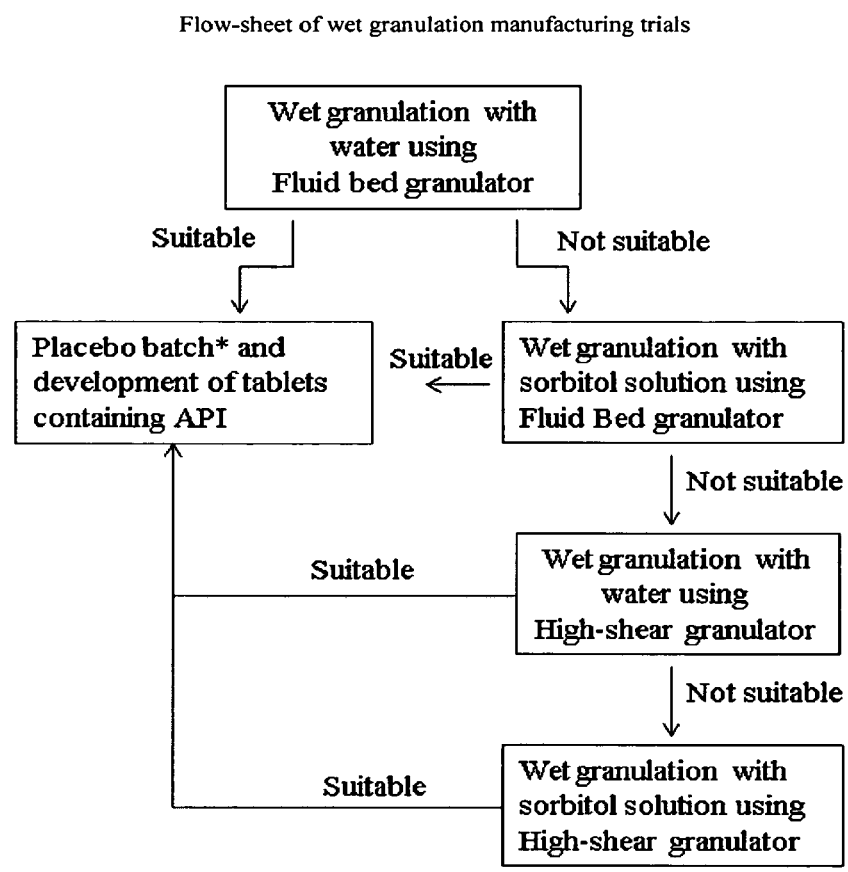
FIG. 2 shows a flow sheet of wet granulation manufacturing trials.

Each saccharide was granulated according to the steps described in the flow-sheet of FIG. 2. At the end of each step the wet granulated saccharide was dried and a compression trial was performed to evaluate if the granulate was suitable for tabletting. Placebo batches were manufactured only for the granulated saccharides with doubtful results of the compression test. The compositions and the relevant analytical results of the placebo trials are reported in Table 23.

Placebo batches were manufactured according to the following steps:
1. Wet granulation of the saccharide with water or sorbitol solution using Fluid Bed or High Shear granulator (see above Flow-sheet of wet granulation manufacturing trials, and table 23)
2. Drying of the wet granulated saccharide in the Fluid Bed granulator or in oven.
3. Sieving the granulated saccharide by using 850 and 710 micron nets.
4. Weighing of all components of the formulation and mixing in a polyethylene bag for 2 minutes.
5. Compression of the powder blend using an eccentric tablet machine equipped with a 10 mm diameter punch.

Avicel PH 112 and magnesium stearate were used as disintegrant and as lubricant, respectively, for all the batches produced.

TABLE 23

Wet granulation. Placebo batches composition and IPC results.

| | Placebo Batches manufactured by Wet Granulation | | | | | |
|---|---|---|---|---|---|---|
| Components | D001T/ 032 (%$_{w/w}$) | D001T/ 034 (%$_{w/w}$) | D001T/ 035 (%$_{w/w}$) | D001T/ 045 (%$_{w/w}$) | D001T/ 051 (%$_{w/w}$) | D001T/ 054 (%$_{w/w}$) |
| Dextrose Anhydrous (Dextrose Anhydrous ST 0.5) | 93.66 | — | — | — | — | — |
| Dextrose Monohydrate (Dextrose Monohydrate) | — | 93.66 | — | — | — | — |

TABLE 23-continued

Wet granulation. Placebo batches composition and IPC results.

| | | | | | | |
|---|---|---|---|---|---|---|
| Mannitol (Pearlitol 200 SD) | — | — | 93.67 | — | — | — |
| D-Melezitose monohydrate | — | — | — | 93.55 | — | — |
| Maltitol (Sweetpearl P200) | — | — | — | — | 93.70 | — |
| Trehalose (Food grade) (Treha 16400) | — | — | — | — | — | 93.72 |
| D-Raffinose Pentahydrate | — | — | — | — | — | — |
| Erythritol (Food grade) (Zerose Etythritol 16954) | — | — | — | — | — | — |
| Fructose (Fructose MS) | | | | | | |
| Xylitol (Xyilisorb 300) | | | | | | |
| Avicel PH 112 | 5.7 | 5.7 | 5.7 | 5.7 | 5.7 | 5.7 |
| Magnesium Stearate | 0.6 | 0.6 | 0.6 | 0.8 | 0.6 | 0.6 |
| Equipment and Binder Solution utilized for saccharide granulation | Fluid Bed Water | High Shear Water | Fluid Bed Water | Fluid Bed Water | Fluid Bed Sorbitol solution | Fluid Bed Sorbitol solution |
| Percentage of sorbitol in the granulate (%$_{w/w}$) | n/a | n/a | n/a | n/a | 1.2 | 1.1 |
| Percentage of water in the granulate (%$_{w/w}$) | 1.03 | 7.93 | 0.20 | 5.08 | 0.20 | 0.22 |

Results of analytical tests performed on tablets

| | | | | | | |
|---|---|---|---|---|---|---|
| Appearance | Complies | Complies | Complies | Complies | Complies | Complies |
| Hardness (N) | 98 | 82 | 277 | 96 | 76 | 60 |

Placebo Batches manufactured by Wet Granulation

| Components | D001T/055 (%$_{w/w}$) | D001T/057 (%$_{w/w}$) | D001T/058 (%$_{w/w}$) | D001T/070 (%$_{w/w}$) | D001T/075 (%$_{w/w}$) |
|---|---|---|---|---|---|
| Dextrose Anhydrous (Dextrose Anhydrous ST 0.5) | — | — | — | | |
| Dextrose Monohydrate (Dextrose Monohydrate) | — | — | — | | |
| Mannitol (Pearlitol 200 SD) | — | — | — | — | |
| D-Melezitose monohydrate | — | — | — | — | |
| Maltitol (Sweetpearl P200) | | | | | |
| Trehalose (Food grade) (Treha 16400) | | | | | |
| D-Raffinose Pentahydrate | 93.72 | | | | |
| Erythritol (Food grade) (Zerose Etythritol 16954) | — | 93.52 | | 93.56 | |
| Fructose (Fructose MS) | | | 93.66 | | |
| Xylitol (Xyilisorb 300) | | | | | 93.71 |
| Avicel PH 112 | 5.7 | 5.8 | 5.7 | 5.8 | 5.7 |
| Magnesium Stearate | 0.6 | 0.7 | 0.6 | 0.7 | 0.6 |
| Equipment and Binder Solution utilized for saccharide granulation | Fluid Bed Sorbitol solution | Fluid Bed Sorbitol solution | High Shear Water | High Shear Water | High Shear Water |
| Percentage of sorbitol in the granulate (%$_{w/w}$) | 1.1 | 1.1 | N/A | N/A | N/A |
| Percentage of water in the granulate (%$_{w/w}$) | 15.40 | 0.22 | 0.13 | 0.40 | 0.19 |

Results of analytical tests performed on tablets

| | | | | | |
|---|---|---|---|---|---|
| Appearance | Complies | Complies | Complies | Not Complies | Not Complies |
| Hardness (N) | 64 | 15 | 30 | N/A | N/A |

API-Containing Batches Manufactured by Wet Granulation with a 1:5 API/Saccharide Weight Ratio Manufacturing trials including a wet granulation process were carried out on all saccharides that turned out to be not suitable for tablet manufacturing by dry granulation or direct compression technologies.

The manufacturing process of these trials performed at laboratory scale is summarized as follow:
1. Wet granulation of the saccharide with water or sorbitol solution using Fluid Bed or High Shear granulator (see above Flow-sheet of wet granulation manufacturing trials, and table 24)
2. Drying of the wet granulated saccharide in the Fluid Bed granulator or in oven
3. Sieving by using 850 and 710 micron nets.
4. Weighing of the API and excipients and mixing in a double polyethylene bag for 5 minutes.
5. Compression of the powder blend using an eccentric tablet machine equipped with a 10 mm diameter punch.

Avicel PH 112 and magnesium stearate were used as disintegrant and as lubricant, respectively, for all the batches produced.

Table 24 and Table 25 list the composition of each API-containing formulation manufactured by wet granulation and the results of the analytical tests performed on both, the final mixtures and the tablets.

The results of the analytical tests performed on the final mixtures and on the finished products are, in the most of the cases, in compliance with the specifications. No degradation occurs during the manufacturing process.

Among the saccharides investigated, only Fructose MS (Galam) is not suitable to be processed by wet granulation: the API-containing batch D001 T/047 has a high friability and the batch D001T/082 shows friability and hardness values out of specifications.

The batches D001 T/060, D001 T/061, D001T/082, D001 T/086 have low values in API assay and for the batches D001T/082 and D001 T/086 the Uniformity of Content does not comply, though the granulate was sieved by using 850 micron and 710 micron nets. This result is probably due to poor powders mixing.

TABLE 24

Wet granulation-API/Saccharide weight ratio 1:5. API-containing batches final mixture composition and analytical results.

| Components | API-containing Batches manufactured by Wet Granulation | | | | | |
|---|---|---|---|---|---|---|
| | D001T/033 ($\%_{w/w}$) | D001T/036 ($\%_{w/w}$) | D001T/037 ($\%_{w/w}$) | D001T/040 ($\%_{w/w}$) | D001T/047 ($\%_{w/w}$) (*) | D001T/059 ($\%_{w/w}$) |
| Bendamustine HCl | 15.7 | 15.7 | 15.7 | 15.7 | 14.9 | 15.7 |
| Dextrose Anhydrous (Anhydrous Dextrose ST 0.5) | 78 | — | — | — | — | — |
| Dextrose Monohydrate G | — | 78 | — | — | — | — |
| Mannitol (Pearlitol 200 SD) | — | — | 78 | — | — | — |
| Lactitol Monohydrate (Lacty M)(Food grade) | — | — | — | 78 | — | — |
| D-Melezitose monohydrate | — | — | — | — | 78.8 | — |
| Maltitol (Sweetpearl P200) | — | — | — | — | — | 78 |
| Trehalose (Food grade) (Treha 16400) | — | — | — | — | — | — |
| D-Raffinose Pentahydrate | — | — | — | — | — | — |
| Erythritol (Food grade) (Zerose Erythritol 16954) | | | | | | |
| Xylitol (Xyilisorb 300) (**) | | | | | | |
| Fructose MS (**) | | | | | | |
| Avicel PH 112 | 5.7 | 5.7 | 5.7 | 5.7 | 5.7 | 5.7 |
| Magnesium Stearate | 0.6 | 0.6 | 0.6 | 0.6 | 0.6 | 0.6 |
| Equipment and Binder Solution utilized for saccharide granulation | Fluid Bed Water | High Shear Water | Fluid Bed Water | Fluid Bed Water | Fluid Bed Water | Fluid Bed Sorbitol solution |
| Percentage of sorbitol in the granulate ($\%_{w/w}$) | N/A | N/A | N/A | N/A | N/A | 1.2 |
| Results of analytical tests performed on final mixtures | | | | | | |
| Flowability (seconds) (Test performed according to EP 6.0, par. 2.9.16) | Not flow (Nozzle 3, diameter = 25.0 mm) | 18.95 (Nozzle 1, diameter = 10.0 mm) | 11.14 (Nozzle 2, diameter = 15.0 mm) | 6.12 (Nozzle 2, diameter = 15.0 mm) | Not flow (Nozzle 3, diameter = 25.0 mm) | 5.12 (Nozzle 2, diameter = 15.0 mm) |
| Observations on manufactured tablets | | | | | | |
| Appearance Stability Study | Complies Suitable for Stability Study | Complies Suitable for Stability Study | Complies Suitable for Stability Study | Complies Suitable for Stability Study | Complies Suitable for Stability Study | Complies Suitable for Stability Study |

TABLE 24-continued

Wet granulation-API/Saccharide weight ratio 1:5. API-containing batches final mixture composition and analytical results.

| | | API-containing Batches manufactured by Wet Granulation | | | | |
|---|---|---|---|---|---|---|
| | Components | D001T/060 (%$_{w/w}$) | D001T/061 (%$_{w/w}$) | D001T/082 (%$_{w/w}$) | D001T/086 (%$_{w/w}$) | D001T/087 (%$_{w/w}$) |
| | Bendamustine HCl | 15.7 | 15.7 | 15.7 | 15.7 | 15.7 |
| | Dextrose Anhydrous (Anhydrous Dextrose ST 0.5) | — | — | — | — | — |
| | Dextrose Monohydrate G | — | — | — | — | |
| | Mannitol (Pearlitol 200 SD) | — | — | — | — | |
| | Lactitol Monohydrate (Lacty M)(Food grade) | — | — | — | — | |
| | D-Melezitose monohydrate | — | — | — | — | |
| | Maltitol (Sweetpearl P200) | | | | | |
| | Trehalose (Food grade) (Treha 16400) | 78 | | | | |
| | D-Raffinose Pentahydrate | — | 78 | | | |
| | Erythritol (Food grade) (Zerose Erythritol 16954) | — | — | 78 | | |
| | Xylitol (Xyilisorb 300) (**) | | | | 78 | |
| | Fructose MS (**) | | | | | 78 |
| | Avicel PH 112 | 5.7 | 5.7 | 5.7 | 5.7 | 5.7 |
| | Magnesium Stearate | 0.6 | 0.6 | 0.6 | 0.6 | 0.6 |
| | Equipment and Binder Solution utilized for saccharide granulation | Fluid Bed Sorbitol solution | Fluid Bed Sorbitol solution | High Shear Sorbitol solution | High Shear Sorbitol solution | High Shear Sorbitol solution |
| | Percentage of sorbitol in the granulate (%$_{w/w}$) | 1.1 | 1.1 | 3.4 | 4.8 | 3.0 |
| | | Results of analytical tests performed on final mixtures | | | | |
| | Flowability (seconds) (Test performed according to EP 6.0, par. 2.9.16) | 6.46 (Nozzle 2, diameter = 15.0 mm) | 5.35 (Nozzle 2, diameter = 15.0 mm) | Not flow (Nozzle 3, diameter = 25.0 mm) | 4.23 (Nozzle 2, diameter = 15.0 mm) | Not flow (Nozzle 3, diameter = 25.0 mm) |
| | | Observations on manufactured tablets | | | | |
| | Appearance | Complies | Complies | Complies | Complies | Not Complies (***) |
| | Stability Study | Suitable for Stability Study | Suitable for Stability Study | Suitable for Stability Study | Suitable for Stability Study | Not Suitable for Stability Study |

(*) This batch contains an excess of A.P.I (5.9%);
(**) It was not possible to investigate granulation step using fluid bed with saccharide solution because these saccharides are not fluidized with air stream;
(***) The final mixture is not suitable for tabletting

TABLE 25

Wet granulation-API/Saccharide weight ratio 1:5. API-containing batches tablets analytical results.

| | Specification | Results of analytical tests performed on tablets | | | | |
|---|---|---|---|---|---|---|
| Analytical Test | Limits | D001T/033 | D001T/036 | D001T/037 | D001T/040 | D001T/047 |
| Identification (HPLC) | Positive | Positive | Positive | Positiw | Positive | Positive |
| Mean Weight (mg/tablet) | Specific for each formulation | 348.52 Limits: 332.5 + 367.5 | 351.56 Limits: 332.5 + 367.5 | 354.06 Limits: 332.5 + 367.5 | 351.98 Limits: 332.5 + 367.5 | 368.66 Limits: 351.5 + 388.5 |
| Content Uniformity (Test performed according to EP 6.0) | Complies | Complies RSD 1.50 | Complies RSD 3.64 | Complies RSD 1.35 | Complies RSD 2.82 | Complies RSD 1.11 |

TABLE 25-continued

Wet granulation-API/Saccharide weight ratio 1:5. API-containing batches tablets analytical results.

| | | | | | | |
|---|---|---|---|---|---|---|
| Assay (%) (HPLC) | 95.0%-105.0% | 101.0 | 98.2 | 98.4 | 98.6 | 101.2 |
| Related substances (%) (HPLC) | | | | | | |
| HP1 | ≤0.5% | 0.08 | 0.08 | 0.09 | 0.08 | 0.10 |
| BM1 Dimer | ≤0.2% | 0.04 | 0.04 | 0.04 | 0.04 | 0.04 |
| BM1EE | ≤0.5% | 0.13 | 0.13 | 0.13 | 0.14 | 0.16 |
| NP1 | ≤0.2% | 0.01 | 0.01 | 0.01 | 0.01 | 0.01 |
| Individual unknown impurity | ≤0.1% | 0.02 | 0.02 | 0.02 | 0.03 | 0.03 |
| Total impurities | ≤1.5% | 0.30 | 0.30 | 0.31 | 0.30 | 0.34 |
| Dissolution Test (Medium: buffer pH = 1.5) | | | | | | |
| (%10 min) | 80% in 30 minutes | 91.9 | 73.9 | 97.1 | 77.0 | 80.9 |
| (%20 min) | | 93.3 | 90.5 | 95.5 | 88.4 | 93.5 |
| (%30 min) | | 91.8 | 89.5 | 93.7 | 87.8 | 92.3 |
| Moisture content (%) | — | 1.15 | 6.58 | 0.59 | 4.48 | 4.14 |
| Hardness (N) | ≥40 N | 68 | 66 | 140 | 46 | 73 |
| Friability N (Test performed according to EP 6.0, per. 2.9.7) | ≤1.0% | 0.5 | 0.5 | 0.2 | 0.6 | Test failure (28.3) |
| Analytical Test | D001T/059 | D001T/060 | D001T/061 | D001T/082 | D001T/086 | D001T/087 |
| Identification (HPLC) | Positive | Positive | Positive | Positive | Positive | N/A |
| Mean Weight (mg/tablet) | 347.49 Limits: 332.5 + 367.5 | 350.37 Limits: 332.5 + 367.5 | 349.04 Limits: 332.5 + 367.5 | 352.09 Limits: 332.5 + 367.5 | 351.78 Limits: 332.5 + 367.5 | N/A |
| Content Uniformity (Test performed according to EP 6.0) | Complies RSD 3.36 | Complies RSD 3.38 | Complies RSD 2.99 | Not complies RSD 31.06 | Not complies RSD 8.39 | N/A |
| Assay (%) (HPLC) | 96.7 | 91.3 | 92.7 | 90.6 | 94.0 | N/A |
| Related substances (%) (HPLC) | | | | | | |
| HP1 | 0.07 | 0.07 | 0.13 | 0.05 | 0.21 | N/A |
| BM1 Dimer | 0.04 | 0.04 | 0.04 | 0.04 | 0.04 | |
| BM1EE | 0.14 | 0.13 | 0.13 | 0.12 | 0.15 | |
| NP1 | 0.01 | 0.01 | 0.01 | 0.01 | 0.02 | |
| Individual unknown impurity | n.d. | 0.01 | 0.02 | 0.02 | 0.04 | |
| Total impurities | 0.26 | 0.26 | 0.33 | 0.24 | 0.49 | |
| Dissolution Test (Medium: buffer pH = 1.5) | | | | | | |
| (%10 min) | 77.5 | 86.3 | 71.4 | 90.5 | 87.2 | N/A |
| (%20 min) | 87.2 | 99.7 | 88.4 | 89.0 | 92.2 | |
| (%30 min) | 86.9 | 99.9 | 87.9 | 87.2 | 89.2 | |
| Moisture content (%) | 0.49 | 7.81 | 12.12 | 0.51 | 0.56 | 0.90 |
| Hardness (N) | 81 | 48 | 71 | 26 | 56 | N/A |
| Friability N (Test performed according to EP 6.0, per. 2.9.7) | 0.4 | 0.4 | 0.3 | Test failure (74) | 0.3 | N/A |

API-Containing Batches Manufactured by Wet Granulation with a 1:2 API/Saccharide Weight Ratio All saccharides previously investigated by wet granulation to manufacture tablets with a 1:5 API/Saccharide weight ratio were also evaluated at a ratio of 1:2.

The fructose was not evaluated at a ratio of 1:2 because the obtained granulate is not suitable for tabletting.

Avicel PH 112 and magnesium stearate were used as disintegrant and as lubricant, respectively, for all the batches produced.

To improve the uniformity of the API content, these API-containing batches were manufactured by applying the following approach:
1. Wet granulation of the saccharide by using procedures previously optimized
2. Preparation of the API-containing mixture
3. Dry granulation of the mixture (Slugs production→Slugs sieving)
4. Tabletting of the obtained mixture by using a 8 mm diameter punch.

For the step 3 (Dry granulation of the mixture) see above.

Table 26 and table 27 report the compositions and the analytical results of the API-containing batches manufactured by using wet granulated saccharides with a API/Saccharide weight ratio of 1:2. Friability is, in the most of the cases, out of specifications. The API/Saccharide weight change does not compromise the technological properties of the D001T/084 batch (Filler: granulated mannitol).

TABLE 26

Wet granulation-A.P.I./Saccharide weight ratio 1:2. API-containing batches final mixture composition and analytical results.

API-containing Batches manufactured by Wet Granulation
API/Saccharide ratio 1:2

| Components | D001T/114 (%$_{w/w}$) | D001T/115 (%$_{w/w}$) | D001T/084 (%$_{w/w}$) | D001T/116 (%$_{w/w}$) | D001T/117 (%$_{w/w}$) | D001T/118 (%$_{w/w}$) | D001T/119 (%$_{w/w}$) | D001T/120 (%$_{w/w}$) | D001T/123 (%$_{w/w}$) | D001T/124 (%$_{w/w}$) |
|---|---|---|---|---|---|---|---|---|---|---|
| Bendamustine HCl | 31.1 | 31.1 | 31.1 | 31.1 | 311 | 31.1 | 31.1 | 31.1 | 31.1 | 31.1 |
| Dextrose Monohydrate G | 62.3 | — | — | — | — | — | — | — | — | — |
| Dextrose Anhydrous (Anhydrous Dextrose ST 0.5) | — | 62.3 | — | — | — | — | — | — | — | — |
| Mannitol (Pearlitol 200 SD) | — | — | 62.3 | — | — | — | — | — | — | — |
| D-Melezitose monohydrate | — | — | — | 62.3 | — | — | — | — | — | — |
| Maltitol (Sweetpearl P200) | — | — | — | — | 62.3 | — | — | — | — | — |
| Trehalose (Food grade) (Treha 16400) | — | — | — | — | — | 62.3 | — | — | — | — |
| D-Raffinose Pentahydrate | — | — | — | — | — | — | 62.3 | — | — | — |
| Erythritol (Food grade) (Zerose Erythritol 16954) | — | — | — | — | — | — | — | 62.3 | — | — |
| Lactitol monohydrate (*) | — | — | — | — | — | — | — | — | 62.3 | — |
| Xylitol (Xyilisorb 300) (**) | — | — | — | — | — | — | — | — | — | 62.3 |
| Avicel PH 112 | 5.9 | 5.9 | 5.9 | 5.9 | 5.9 | 5.9 | 5.9 | 5.9 | 5.9 | 5.9 |
| Magnesium Stearate | 0.7 | 0.7 | 0.7 | 0.7 | 0.7 | 0.7 | 0.7 | 0.7 | 0.7 | 0.7 |
| Equipment and Binder Solution utilized for saccharide granulation | High Shear Water | Fluid Bed Water | Fluid Bed Water | Fluid Bed Water | Fluid Bed Sorbitol solution | Fluid Bed Sorbitol solution | Fluid Bed Sorbitol solution | High Shear Sorbitol solution | Fluid Bed Water | High Shear Sorbitol solution |
| Percentage of sorbitol in the granulate (%$_{w/w}$) | N/A | N/A | N/A | N/A | 1.2 | 1.1 | 1.1 | 3.4 | N/A | 4.8 |
| Results of analytical Tests performed on final mixtures | | | | | | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) |

(*) As the lactitol used to develop the previous formulation (API/Saccharide weight ratio 1:5) is no longer commercially available, this batch was manufactured by using lactitol purchased by new manufacturer (Lactitol MC by Danisco).

TABLE 27

Wet granulation-A.P.I./Saccharide weight ratio 1:2. API-containing batches tablets analytical results.

| Analytical Test | Specification Limits | Results of analytical tests performed on tablets | | | | |
|---|---|---|---|---|---|---|
| | | D001T/114 | D001T/115 | D001T/084 | D001T/116 | D001T/117 |
| Identification (HPLC) | Positive | Positive | Positive | Positive | Positive | Positive |
| Mean Weight (mg/tablet) | Specific for each formulation | 178.67 Limits: 168.2 + 185.9 | 184.41 Limits: 168.2 + 185.9 | 177.14 Limits: 168.2 + 185.9 | 174.81 Limits: 168.2 + 185.9 | 178.70 Limits: 168.2 + 185.9 |
| Content Uniformity (Test performed according to EP 6.0) | Complies | Complies RSD 2.3 | Complies RSD 2.9 | Complies RSD 2.40 | Complies RSD 3.4 | Complies RSD 4.0 |
| Assay (%) (HPLC) | 95.0%-105.0% | 96.9 | 103.5 | 98.8 | 94.8 | 98.5 |
| Related substances (%) (HPLC) | | | | | | |
| HP1 | ≤0.50% | 0.07 | 0.14 | 0.09 | 0.07 | 0.08 |
| BM1 Dimer | ≤0.20% | 0.03 | 0.04 | 0.04 | 0.04 | 0.04 |
| BM1EE | ≤0.50% | 0.14 | 0.16 | 0.13 | 0.13 | 0.15 |
| NP1 | ≤0.20% | 0.01 | 0.01 | 0.01 | 0.01 | 0.01 |
| Individual unknown impurity | ≤0.10% | n.d. | n.d. | n.d. | 0.01 | 0.02 |
| Total impurities | ≤1.50% | 0.25 | 0.35 | 0.27 | 0.27 | 0.33 |
| Dissolution Test (Medium: buffer pH = 1.5) | | | | | | |
| (%10 min) | 80% in 30 min | 71.7 | 85.3 | 94.4 | 65.6 | 49.8 |
| (%20 min) | | 93.5 | 91.7 | 93.8 | 83.6 | 69.2 |

TABLE 27-continued

Wet granulation-A.P.I./Saccharide weight ratio 1:2. API-containing batches tablets analytical results.

| | | | | | | |
|---|---|---|---|---|---|---|
| (%30 min) | | 94.5 | 91.8 | 92.6 | 88.8 | 88.8 |
| Moisture content (%) | — | 5.4 | 1.1 | 1.5 | 3.2 | 0.5 |
| Hardness (N) | ≥40 N | 47 | 46 | 67 | 49 | 41 |
| Friability (%) (Test performed according to EP 6.0) | ≤1.0% | Test failure (9.0) | Test failure (41.3) | 0.4 | Test failure (60.0) | 1.2 |

| | | Results of analytical tests performed on tablets | | | | |
|---|---|---|---|---|---|---|
| | Analytical Test | D001T/118 | D001T/119 | D001T/120 | D001T/123 | D001T/124 |
| | Identification (HPLC) | Positive | Positive | Positive | Positive | Positive |
| | Mean Weight (mg/tablet) | 179.86 Limits: 168.2 + 185.9 | 177.30 Limits: 168.2 + 185.9 | 183.26 Limits: 168.2 + 185.9 | 180.33 Limits: 168.2 + 185.9 | 173.38 Limits: 168.2 + 185.9 |
| | Content Uniformity (Test performed according to EP 6.0) | Complies RSD 1.7 | Complies RSD 1.4 | Not Complies RSD 7.4 | Not Complies RSD 11.3 | Complies RSD 2.7 |
| | Assay (%) (HPLC) | 98.0 | 96.9 | 100.4 | 98.0 | 96.7 |
| | Related substances (%) (HPLC) | | | | | |
| | HP1 | 0.06 | 0.11 | 0.09 | 0.05 | 0.06 |
| | BM1 Dimer | 0.04 | 0.04 | 0.04 | 0.04 | 0.03 |
| | BM1EE | 0.15 | 0.14 | 0.14 | 0.15 | 0.13 |
| | NP1 | 0.01 | 0.01 | 0.01 | 0.01 | 0.01 |
| | Individual unknown impurity | 0.02 | 0.02 | 0.04 | 0.03 | 0.03 |
| | Total impurities | 0.32 | 0.34 | 0.37 | 0.32 | 0.29 |
| | Dissolution Test (Medium: buffer pH = 1.5) | | | | | |
| | (%10 min) | 48.2 | 68.2 | 81.9 | 51.4 | 58.2 |
| | (%20 min) | 74.5 | 92.5 | 84.4 | 71.9 | 80.4 |
| | (%30 min) | 84.8 | 92.5 | 84.5 | 82.2 | 86.3 |
| | Moisture content (%) | 6.3 | 9.4 | 0.8 | 3.6 | 0.5 |
| | Hardness (N) | 44 | 50 | 18 | 43 | 45 |
| | Friability (%) (Test performed according to EP 6.0) | Test failure (41.1) | Test failure (16.8) | Test failure (97.4) | Test failure (16.0) | 0.8 |

Effect of the API/Mannitol Weight Ratio

Mannitol based tablets were manufactured investigating the following API/mannitol ratios: (1:0.01, 1:0.1, 1:0.5, 1:1.7, 1:4, 1:5, 1:6 and 1:10). The formulation with a 1:5 API/mannitol weight ratio (standard formulation) was reported above.

For the production of these batches Avicel PH 112 and magnesium stearate were used as disintegrant and as lubricant respectively. Regarding the manufacturing process, for the 1:1.7, 1:4, and 1:6 ratios, wet granulated mannitol, Bendamustine Hydrochloride and excipients were accurately weighed and mixed in a double polyethylene bag for 5 minutes. For batch D001T/110 (1:10 ratio) a premix was performed. In this case, Bendamustine Hydrochloride was mixed, for 5 min, with half quantity of the excipients mixture. Then, the obtained mixture was added to the remaining quantity of the excipients and mixed for additional 5 minutes. The final mixture was tabletted using the tabletting machine equipped with a suitable punch (8 mm diameter punch for 1:1, 1:1.7 and 1:2 ratios, 10 mm in the case of 1:4 and 1:6 ratios, 12 mm for 1:7 ratio and 14 mm for 1:10 ratio).

With regard to the 1:0.01, 1:0.1, 1:0.5 ratios, we have applied the manufacturing process reported above (wet granulation of the saccharide and subsequent dry granulation), to improve the API content uniformity. The obtained mixture was tabletted using a 6 mm diameter punch.

The following tables (Table 28 and Table 29) summarize the compositions and the analytical results of the API-containing formulations manufactured to study the effects of the different API/Mannitol ratios. The batches D001T/111, D001T/083 and D001T/106 showed high friability and for the batches D001T/106, D001T/108 and D001T/109 the Uniformity of Content did not comply deviating from data trends previously obtained. This result may be due to the fact that these batches were produced using a new lot of Bendamustine HCl (Lot number: F08-05873) that may have different physical properties.

TABLE 28

Effect of the A.P.I./Mannitol weight ratio. API-containing batches final mixture composition A.P.I./Mannitol Ratio Study

| | D001T/ 113 (%w/w) | D001T/ 112 (%w/w) | D001T/ 111 (%w/w) | D001T/ 083 (%w/w) | D001T/ 106 (%w/w) | D001T/ 084 (%w/w) | D001T/ 108 (%w/w) | D001T/ 037 (%w/w) | D001T/ 109 (%w/w) | D001T/ 085 (%w/w) | D001T/ 110 (%w/w) |
|---|---|---|---|---|---|---|---|---|---|---|---|
| A.P.I./Saccharide Ratio | 1:0.01 (*) | 1:0.1 (*) | 1:0.5 (*) | 1:1 | 1:1.7 | 1:2 | 1:4 | 1:5 | 1:6 | 1:7 | 1:10 |
| Bendamustine HCl | 55.1 | 55.1 | 55.1 | 44.1 | 34.4 | 31.1 | 18.7 | 15.7 | 13.4 | 11.9 | 8.6 |
| Mannitol Granulated (Pearlitol 200 SD) | 0.55 | 5.51 | 27.6 | 44.1 | 58.5 | 62.3 | 74.7 | 78.0 | 80.7 | 82.9 | 86.1 |
| Avicel PH 112 | 43.7 | 38.7 | 16.6 | 11.1 | 6.4 | 5.9 | 5.9 | 5.7 | 5.3 | 4.6 | 4.6 |
| Magnesium Stearate | 0.7 | 0.7 | 0.7 | 0.7 | 0.7 | 0.7 | 0.7 | 0.6 | 0.6 | 0.6 | 0.7 |
| Batch number of Bendamustine HCl | F08-03755 | F08-03755 | F08-03755 | F08-03755 | F08-05873 | F08-03755 | F8-05873 | F08-03755 | F8-05873 | F08-03755 | F08-03755 |
| Results of analytical tests performed on final mixtures ||||||||||||
| Flowability (seconds) (Test performed according to EP 6.0, par. 2.9.16) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | Not flow (Nozzle 3, diameter = 25.0 mm) | 5.20 (Nozzle 3, diameter = 25.0 mm) | 11.14 (Nozzle 2, diameter = 15.0 mm) | 2.59 (Nozzle 3, diameter = 25.0 mm) | 10.90 (Nozzle 2, diameter = 15.0 mm) | 10.06 (Nozzle 2, diameter = 15.0 mm) |

(*) Batches manufactured by using the experimental approach reported above
☐ Standard formulation 1:5 API/Saccharide weight ratio

TABLE 29

Effect of the A.P.I./Mannitol weight ratio study. API-containing batches tablets analytical results.

| | Specification | Results of analytical tests performed on tablets | | | | |
|---|---|---|---|---|---|---|
| Analytical Test | Limits | D001T/113 | D001T/112 | D001T/111 | D001T/083 | D001T/106 |
| Identification (HPLC) | Positive | Positive | Positive | Positive | Positive | Positive |
| Mean Weight (mg/tablet) | Specific for each formulation | 100.28 Limits: 95 + 105 | 104.51 Limits: 95 + 105 | 95.95 Limits: 95 + 105 | 126.76 Limits: 118.75 + 131.3 | 163.85 Limits: 152.0 + 168.0 |
| Content Uniformity (Test performed according to EP 6.0) | Complies | Complies RSD 2.7 | Complies RSD 3.2 | Complies RSD 3.7 | Complies RSD 2.77 | Not Complies RSD 14.24 |
| Assay (%) (HPLC) | 95.0%-105.0% | 101.6 | 104.1 | 95.4 | 99.3 | 96.8 |
| Related substances (%) (HPLC) | | | | | | |
| HP1 | ≤0.50% | 0.07 | 0.11 | 0.06 | 0.09 | 0.09 |
| BM1 Dimer | ≤0.20% | 0.04 | 0.04 | 0.04 | 0.04 | 0.04 |
| BM1EE | ≤0.50% | 0.15 | 0.16 | 0.15 | 0.14 | 0.12 |
| NPI | ≤0.20% | 0.01 | 0.01 | 0.01 | 0.01 | 0.01 |
| Individual unknown impurity | ≤0.10% | n.d. | n.d. | n.d. | 0.02 | n.d. |
| Total impurities | ≤1.50% | 0.27 | 0.32 | 0.26 | 0.31 | 0.26 |
| Dissolution Test (Medium: buffer pH = 1.5) | | | | | | |
| (%10 min) | 80% in 30 min | 71.8 | 81.3 | 86.7 | 80.6 | 75.7 |
| (%20 min) | | 77.5 | 88.0 | 92.1 | 83.1 | 81.8 |
| (%30 min) | | 80.0 | 87.5 | 95.2 | 81.3 | 84.1 |
| Moisture content (%) | — | 2.3 | 2.1 | 1.1 | 0.8 | 0.5 |
| Hardness (N) | ≥40 N | 88 | 85 | 67 | 63 | 70 |
| Friability (%) (Test performed according to EP 6.0) | ≤1.0% | 0.7 | 0.9 | Test failure (6.1) | Test failure (5.2) | Test failure (18.8) |

| | Results of analytical tests performed on tablets | | | | | |
|---|---|---|---|---|---|---|
| Analytical Test | D001T/084 | D001T/108 | D001T/037 | D001T/109 | D001T/085 | D001T/110 |
| Identification (HPLC) | Positive | Positive | Positive | Positive | Positive | Positive |

TABLE 29-continued

Effect of the A.P.I./Mannitol weight ratio study. API-containing batches tablets analytical results.

| | | | | | | |
|---|---|---|---|---|---|---|
| Mean Weight (mg/tablet) | 177.14 Limits: 168.2 + 185.9 | 299.05 Limits: 280.3 + 309.8 | 354.06 Limits: 332.5 + 367.5 | 410.0 Limits: 389.5 + 430.5 | 469.55 Limits: 441.8 + 488.3 | 646.24 Limits: 608 + 672 |
| Content Uniformity (Test performed according to EP 6.0) | Complies RSD 2.40 | Not Complies RSD 8.63 | Complies 1.35 | Not Complies RSD 8.33 | Complies RSD 2.79 | Complies RSD 2.6 |
| Assay (%) (HPLC) | 98.8 | 97.1 | 98.4 | 97.1 | 95.1 | 99.4 |
| Related substances (%) (HPLC) | | | | | | |
| HP1 | 0.09 | 0.09 | 0.09 | 0.06 | 0.12 | 0.07 |
| BM1 Dimer | 0.04 | 0.04 | 0.04 | 0.04 | 0.03 | 0.04 |
| BM1EE | 0.13 | 0.13 | 0.13 | 0.13 | 0.14 | 0.14 |
| NPI | 0.01 | 0.01 | 0.01 | 0.05 | 0.01 | 0.01 |
| Individual unknown impurity | n.d. | n.d. | 0.02 | n.d. | 0.03 | n.d. |
| Total impurities | 0.27 | 0.27 | 0.31 | 0.28 | 0.33 | 0.26 |
| Dissolution Test (Medium: buffer pH = 1.5) | | | | | | |
| (%10 min) | 94.4 | 90.1 | 97.1 | 91.4 | 96.7 | 97.7 |
| (%20 min) | 93.8 | 89.8 | 95.5 | 91.1 | 94.6 | 97.2 |
| (%30 min) | 92.6 | 88.4 | 93.7 | 90.6 | 92.8 | 96.3 |
| Moisture content (%) | 1.5 | 0.4 | 0.6 | 0.5 | 0.4 | 0.6 |
| Hardness (N) | 67 | 226 | 140 | 227 | 181 | 91 |
| Friability (%) (Test performed according to EP 6.0) | 0.4 | 0.3 | 0.2 | 0.5 | 0.3 | 0.9 |

☐ Standard formulation 1:5 API/Saccharide weight ratio

Saccharides Combination Study

Table 30 and Table 31 report the results concerning the saccharide combination study.

The following combinations were investigated:
—Monosaccharide/Disaccharide 1:1
  (*)Mannitol (Pearlitol 200 SD)/Lactose Anhydrous (SuperTab 21 AN)
  Sorbitol (Neosorb P60W)/Maltose (Sunmalt S)
—Oligosaccharide/Monosaccharide 1:1
  (*)D-Melezitose monohydrate/(*)Dextrose anhydrous ST 0.5
  (*)Raffinose Pentahydrate granulated/(*)Mannitol granulated (Pearlitol 200 SD)
—Oligosaccharide/Disaccharide 1:1
  (*)Raffinose Pentahydrate granulated/Lactose Monohydrate (Supertab 14SD)
  β-Ciclodextrine (Kleptose DC)/Sucrose (EV Saccharide)

(*) These saccharides were granulated by wet granulation (see page 32)

The manufacturing process consisted in direct compression of the unprocessed or granulated saccharide.

By using Avicel PH 112 and magnesium stearate as disintegrant and as lubricant, respectively, these batches were manufactured performing the following steps:

1. The saccharides (or the granulated saccharide), Bendamustine Hydrochloride and excipients were accurately weighed and mixed in a double polyethylene bag for 5 minutes.
2. The obtained mixture was tabletted by using a 10 mm diameter punch.

TABLE 30

Saccharides Combination Study. API-containing batches final mixture composition and analytical results.

| | Saccharide Combination Study API-containing Batches | | | | | |
|---|---|---|---|---|---|---|
| Components | D001T/049 (%$_{w/w}$) | D001T/074 (%$_{w/w}$) | D001T/100 (%$_{w/w}$) | D001T/101 (%$_{w/w}$) | D001T/102 (%$_{w/w}$) | D001T/103 (%$_{w/w}$) |
| Bendamustine HCl | 14.89 | 15.74 | 15.74 | 15.74 | 15.74 | 15.74 |
| Saccharide combination | | | | | | |
| Oligosaccharide/Monosaccharide 1:1 | | | | | | |
| D-Melezitose monohydrate/Dextrose anhydrous ST 0.5 | 78.81 | — | — | — | — | — |
| Raffinose Pentahydrate/Mannitol (Pearlitol 200 SD) | — | — | — | — | 77.96 | — |
| Saccharide combination | | | | | | |
| Oligosaccharide/Disaccharide 1:1 | | | | | | |
| Raffinose Pentahydrate/Lactose Monohydrate (Supertab 14SD) | — | — | — | — | — | 77.96 |

TABLE 30-continued

Saccharides Combination Study. API-containing batches final mixture composition and analytical results.

| Components | Saccharide Combination Study API-containing Batches | | | | | |
|---|---|---|---|---|---|---|
| | D001T/049 (%$_{w/w}$) | D001T/074 (%$_{w/w}$) | D001T/100 (%$_{w/w}$) | D001T/101 (%$_{w/w}$) | D001T/102 (%$_{w/w}$) | D001T/103 (%$_{w/w}$) |
| β-Ciclodextrine (Kleptose DC)/Sucrose (EV Saccharide) | — | — | — | 77.96 | — | — |
| Saccharide combination Monosaccharide/Disaccharide 1:1 | | | | | | |
| Sorbitol (Neosorb P60W)/Maltose (Sunmalt S) | — | — | 77.96 | — | — | — |
| Mannitol (Pearlitol 200 SD)/Anhydrous Lactose (SuperTab 21 AN) | — | 77.96 | — | — | — | — |
| Avicel PH 112 | 5.70 | 5.70 | 5.70 | 5.70 | 5.70 | 5.70 |
| Magnesium Stearate | 0.60 | 0.60 | 0.60 | 0.60 | 0.60 | 0.60 |
| | Results of analytical tests performed on final mixtures | | | | | |
| Flowability (seconds) (Test performed according to EP 6.0, par. 2.9.16) | Not flow (Nozzle 3, diameter = 25.0 mm) | Not flow (Nozzle 3, diameter = 25.0 mm) | 5.24 (Nozzle 3, diameter = 25.0 mm) | 5.25 (Nozzle 3, diameter = 25.0 mm | Not flow (Nozzle 3, diameter = 25.0 mm | Not flow (Nozzle 3, diameter = 25.0 mm |

TABLE 31

Saccharide Combination Study. API-containing batches tablets analytical results.

| Analytical Test | Specification Limits | Results of analytical tests performed on tablets | | | | | |
|---|---|---|---|---|---|---|---|
| | | D001T/049 | D001T/074 | D001T/100 | D001T/101 | D001T/102 | D001T/103 |
| Identification (HPLC) | Positive | Positive | Positive | Positive | Positive | Positive | Positive |
| Mean Weight (mg/tablet) | Specific for each formulation | 365.96 351.5 + 388.5 | 346.06 332.5 + 367.5 | 351.56 332.5 + 36.5 | 349.60 332.5 + 367.5 | 354.13 332.5 + 367.5 | 348.83 332.5 + 367.5 |
| Content Uniformity (Test performed according to EP 6.0) | Complies | Not complies RSD 5.55 | Complies RSD 1.41 | Not Complies RSD 4.50 | Complies RSD 1.51 | Complies RSD 4.73 | Complies RSD 1.46 |
| Assay (%) (HPLC) | 95.0%-105.0% | 96.7 | 95.1 | 97.5 | 97.6 | 97.9 | 98.9 |
| Related substances (%) (HPLC) | | | | | | | |
| HP1 | ≤0.50% | 0.10 | 0.06 | 0.06 | 0.12 | 0.09 | 0.09 |
| BM1 Dimer | ≤0.20% | 0.04 | 0.03 | 0.04 | 0.04 | 0.04 | 0.04 |
| BM1EE | ≤0.50% | 0.15 | 0.13 | 0.12 | 0.12 | 0.12 | 0.12 |
| NP1 | ≤0.20% | 0.01 | 0.01 | 0.01 | 0.01 | 0.01 | 0.01 |
| Individual unknown impurity | ≤0.10% | 0.03 | n.d. | 0.01 | 0.02 | n.d. | 0.02 |
| Total impurities | ≤1.50% | 0.33 | 0.23 | 0.24 | 0.31 | 0.26 | 0.28 |
| Dissolution Test (Medium: buffer pH = 1.5) | | | | | | | |
| (%10 min) | 80% in 30 min | 76.3 | 73.1 | 62.9 | 65.4 | 89.6 | 55.7 |
| (%20 min) | | 93.8 | 97.4 | 86.1 | 89.4 | 91.1 | 87.6 |
| (%30 min) | | 92.7 | 99.2 | 91.7 | 93.4 | 89.8 | 88.9 |
| Moisture content (%) | — | 2.70 | 0.60 | 2.77 | 5.66 | 5.38 | 8.12 |
| Hardness (N) | ≥40 N | 73 | 147 | 216 | 144 | 93 | 118 |
| Friability (%) (Test performed according to EP 6.0) | ≤1.0% | 0.4 | 0.1 | 0.1 | 0.2 | Test failure (26.4) | 0.2 |

In general, the tablets manufactured for the saccharides combination studies show good properties. However, the batch D001T/102 (Raffinose Pentahydrate/Mannitol (Pearlitol 200 SD)), show high friability and the batches D001T/100 and D001T/049 are non homogeneous in API content.

Example 14. Freeze Dried Bendamustine HCl (Ribomustin) and Bendamustine HCl/Mannitol Tablets (Api/Saccharide Weight Ratio 1:1.2)

Tablets containing bendamustine hydrochloride/mannitol in a weight ratio of 1:1.2 were prepared by using either freeze dried material obtained from the commercially available product for intravenous application (Ribomustin®) or using wet granulated mannitol and Bendamustine HCl.

The manufacturing processes were performed according to the following experimental operations: the freeze dried powder was removed from the Ribomustin® vials and was sieved using a 850 micron net. The obtained powder and the lubricant (magnesium stearate) were accurately weighed and mixed in a polyethylene bag for 5 minutes. The mixture was slowly transferred in the pressing chamber of the tabletting machine and was manually pressed by using an 8 mm diameter punch in order to obtain small slugs. The slugs were sieved using a 850 micron net and the obtained granulate was manually pressed using a 8 mm diameter punch.

Bendamustine HCl/mannitol tablets were manufactured applying the same operating procedures as described above in this example.

The composition of the formulations is reported in table 32.

TABLE 32

Ribomustin and bendamustine/mannitol tablets. API-containing batches final mixture composition.

| | Ribomustin and bendamustine/mannitol tablets | |
|---|---|---|
| | D001T/125 (%w/w) | D001T/126 (%w/w) |
| A.P.I./Saccharide Ratio | 1:1.2 | 1:13 |
| Ribomustin Freeze-dried(*) | 99.36 | |
| Bendamustine HCl | | 45.16 |
| Mannitol Granulated (Pearlitol 200 SD) | | 54.20 |
| Magnesium Stearate | 0.64 | 0.64 |
| Batch number of Bendamustine HCl | | F08-03755 |
| Flowability (seconds) (Test performed according to EP 6.0, par. 2.9.16) | N/A | N/A |

(*)Corresponding to 45.16% of Bendamustine HCl and 54.20% of Mannitol

Table 33 reports the data concerning the comparison between the tablets obtained using the freeze dried bendamustine hydrochloride/mannitol mixture and the non freeze-dried bendamustine hydrochloride/mannitol mixture.

TABLE 33

Ribomustin and bendamustine/mannitol tablets. API-containing batches tablets analytical results.

| | Specification | Results of analytical tests performed on tablets | |
|---|---|---|---|
| Analytical Test | Limits | D001T/125 | D001T/126 |
| Identification (HPLC) | Positive | Positive | Positive |
| Mean Weight (mg/tablet) | Specific for each formulation | 123.45 Limits: 115.9 ÷ 128.1 RSD 6.02 | 121.79 Limits: 115.9 ÷ 128.1 RSD 2.88 |
| Content Uniformity (Test performed according to EP 6.0) | Complies | Complies RSD 4.05 | Complies RSD 3.35 |
| Assay (%) (HPLC) | 95.0%-105.0% | 98.6 | 99.5 |
| Related substances (%) (HPLC) | | | |
| HP1 | ≤0.50% | 1.03 | 0.08 |
| BM1 Dimer | ≤0.20% | 0.19 | 0.04 |
| BM1EE | ≤0.50% | 0.19 | 0.14 |
| NP1 | ≤0.20% | 0.01 | 0.01 |
| Individual unknown impurity | ≤0.10% | 0.03 | n.d. |
| Total impurities | ≤1.50% | 1.50 | 0.27 |
| Dissolution Test (Medium: buffer pH = 1.5) | | | |
| (% 10 min) | 80% in 30 min | 93.3 | 57.7 |
| (% 20 min) | | 94.6 | 80.0 |
| (% 30 min) | — | 93.0 | 89.9 |
| Moisture content (%) | | 1.61 | 0.21 |
| Hardness (N) | ≥40 N | 61 | 44 |
| Friability (%) (Test performed according to EP 6.0) | ≤1.0% | N/A | Test failure (15.6) |

Taking as reference target the impurity profile of the Bendamustine Hydrochloride API(see specification limits in the table), batch D001T/125 showed an out of specification value for HP1 impurity. The results of the dissolution test highlight that, although after 10 minutes the dissolution profile of the tablets, containing the freeze-dried bendamustine hydrochloride/mannitol mixture is faster, for both formulations, after 30 minutes the dissolution is in compliance with the current specifications. The friability is out of specification for batch D001T/126, whereas the test was not performed for batch D001T/125 due to lack of sufficient amounts of material.

INDUSTRIAL APPLICABILITY

The compositions according to the present invention show many advantages. They can be easily used by the patient without assistance of supervisory medical staff Hence the time-consuming trips to the hospital may become obsolete, thereby increasing the patient compliance.

Since the dosage forms are solid, they can be swallowed as such, which means that the patient does not need to wait until dissolution of the active ingredient has been achieved. Further due to the good stability of the dosage forms they can be easily stored at room temperature and without the need of any special storage conditions.

By using the dosage forms according to the present invention, a considerable reduction of the volume of the dosage form may be achieved. The reduced size is desirable both from a manufacturing and handling standpoint and patient compliance.

Pharmaceutical compositions show a high dissolution in vitro reducing the degradation of bendamustine in vivo, thus resulting in an improved bioavailability of the bendamustine in vivo.

The invention claimed is:

1. A pharmaceutical composition in a stable solid dosage form formulated for oral administration, the composition comprising non-freeze-dried bendamustine or a pharmaceutically acceptable ester or salt thereof as an active ingredient, and a pharmaceutically acceptable excipient consisting of mannitol,
wherein the ratio by weight of the active ingredient to the excipient is in the range of 1:2-7 or is 1:10, and the composition is in the form of tablet.

2. The pharmaceutical composition of claim 1, wherein the ratio by weight of the active ingredient to the excipient is 1:2-4.

3. The pharmaceutical composition according to claim 1, wherein the tablet is provided with a coating.

4. The pharmaceutical composition according to claim 1, wherein the active ingredient is bendamustine hydrochloride.

5. The pharmaceutical composition according to claim 1, which comprises 10 to 1000 mg of the active ingredient and 30 to 5000 mg of the pharmaceutically acceptable excipient.

6. The pharmaceutical composition according to claim 1, which further comprises a pharmaceutically acceptable lubricant, filler and/or disintegrant.

7. The pharmaceutical composition according to claim 1, wherein the composition shows a dissolution of the bendamustine of at least 60% in 10 minutes, 70% in 20 minutes and 80% in 30 minutes, as measured with a paddle apparatus at 50 rpm according to the European Pharmacopoeia in 500 ml of a dissolution medium at a pH of 1.5.

8. A method of treating a disease in a human comprising orally administering an effective amount of the composition according to claim 1, wherein the disease is selected from the group consisting of chronic lymphocytic leukemia, acute lymphocytic leukaemia, chronic myelocytic leukaemia acute myelocytic leukaemia, Hodgkin's disease, non-Hodgkin's lymphoma, multiple myeloma, breast cancer, ovary cancer, small cell lung cancer, non-small cell lung cancer, and an autoimmune disease.

9. The method according to claim 8, wherein the composition is administered in combination with at least one further active agent, and said further active agent is given prior, concurrently, or subsequently to the administration of the pharmaceutical composition.

10. The method according to claim 9, wherein the further active agent is an antibody specific for CD20, an anthracyclin derivative, a vinca alkaloid or a platin derivative.

11. The method according to claim 10, wherein the antibody specific for CD20 is rituximab, wherein the anthracyclin derivative is doxorubicin or daunorubicin, wherein the vinca alkaloid is vincristine and wherein the platin derivative is cisplatin or carboplatin.

12. The method according to claim 8, wherein the administration is in combination with at least one corticosteroid, wherein said corticosteroid is given prior, concurrently, or subsequently to the administration of the pharmaceutical composition.

13. The method according to claim 12, wherein the corticosteroid is prednisone or prednisolone.

14. A pharmaceutical composition in a stable solid dosage form formulated for oral administration, the composition comprising non-lyophilized bendamustine or a pharmaceutically acceptable ester, or salt thereof as an active ingredient, and one pharmaceutically acceptable excipient,
wherein the one pharmaceutically acceptable excipient is an excipient selected from the group consisting of maltitol, xylitol, sorbitol, and sucrose 97%+maltodextrin 3%,
wherein the ratio by weight of the active ingredient to the excipient is in the range of 1:2-5 and the composition is in the form of a tablet, a granulate, or a pill.

15. The pharmaceutical composition according to claim 14, wherein the composition is in the form of tablet.

16. The pharmaceutical composition according to claim 14, wherein the composition is in the form of a granulate.

17. The pharmaceutical composition according to claim 14, wherein the composition is in the form of a pill.

18. The pharmaceutical composition according to claim 6, wherein the disintegrant is microcrystalline cellulose and the lubricant is magnesium sterate.

* * * * *